(12) United States Patent
Bluecher et al.

(10) Patent No.: US 11,103,340 B2
(45) Date of Patent: *Aug. 31, 2021

(54) BIO-SELECTIVE SURFACE TEXTURES

(71) Applicant: BVW Holding AG, Cham (CH)

(72) Inventors: Lukas Bluecher, Eurasburg (DE); Michael Milbocker, Holliston, MA (US)

(73) Assignee: BVW HOLDING AG, Cham (CH)

( * ) Notice: Subject to any disclaimer, the term of this patent is extended or adjusted under 35 U.S.C. 154(b) by 296 days.

This patent is subject to a terminal disclaimer.

(21) Appl. No.: 15/846,200

(22) Filed: Dec. 18, 2017

(65) Prior Publication Data

US 2018/0168794 A1 Jun. 21, 2018

Related U.S. Application Data

(63) Continuation of application No. 13/745,406, filed on Jan. 18, 2013, now Pat. No. 10,130,459.

(Continued)

(51) Int. Cl.
*A61F 2/02* (2006.01)
*A61L 27/50* (2006.01)
(Continued)

(52) U.S. Cl.
CPC ............ *A61F 2/02* (2013.01); *A61F 2/0063* (2013.01); *A61F 2/0077* (2013.01); *A61L 27/34* (2013.01);
(Continued)

(58) Field of Classification Search
CPC ........ A61F 2/02; A61F 2/0077; A61F 2/0063; A61F 2002/0086; A61F 2002/009;
(Continued)

(56) References Cited

U.S. PATENT DOCUMENTS 6,994,045 B2 2/2006 Paszkowski
7,419,615 B2 9/2008 Strauss
(Continued)

FOREIGN PATENT DOCUMENTS

CN 102834124 A 12/2012
WO 1996018498 6/1996
(Continued)

OTHER PUBLICATIONS

Gross, M. et al., "Fall and rise of small droplets on rough hydrophobic substrates," EPL 88 (2009) 26002.
(Continued)

*Primary Examiner* — Richard G Louis
(74) *Attorney, Agent, or Firm* — Patterson Intellecutal Property Law, P.C.; Ryan D. Levy; Mark A. Kilgore

(57) ABSTRACT

Bio-selective textured surfaces are described which mediate foreign body response, bacterial adhesion, and tissue adhesion on devices implanted in a mammalian body. Hierarchical levels of texture, some capable of establishing a Wenzel state others a Cassie state, are employed to interface with living structures, either to promote or discourage a particular biological response/interaction. Since a gaseous state is traditionally required to establish a Cassie or Wenzel state, and gases do not remain long in living tissue, described are tissue/device interactions analogous to the above states with the component normally represented by a gas replaced by a bodily constituent, wherein separation of tissue constituents develops and a desired interaction state evolves.

19 Claims, 10 Drawing Sheets

Related U.S. Application Data

(60) Provisional application No. 61/589,907, filed on Jan. 11, 2013.

(51) Int. Cl.
  *A61L 27/56* (2006.01)
  *A61F 2/00* (2006.01)
  *A61L 27/34* (2006.01)
  *A61L 31/10* (2006.01)
  *A61L 31/14* (2006.01)

(52) U.S. Cl.
  CPC ............... *A61L 27/50* (2013.01); *A61L 27/56* (2013.01); *A61L 31/10* (2013.01); *A61L 31/14* (2013.01); *A61L 31/146* (2013.01); *A61F 2002/009* (2013.01); *A61F 2002/0086* (2013.01); *A61F 2210/0004* (2013.01); *A61L 2400/18* (2013.01)

(58) Field of Classification Search
  CPC ........... A61F 2210/0004; A61L 31/146; A61L 31/14; A61L 27/34; A61L 31/10; A61L 27/50; A61L 27/56; A61L 2400/18
  See application file for complete search history.

(56) References Cited

U.S. PATENT DOCUMENTS

| | | |
|---|---|---|
| 7,887,736 B2 | 2/2011 | Lee et al. |
| 2003/0147932 A1 | 8/2003 | Nun et al. |
| 2004/0224008 A1 | 11/2004 | Zhang |
| 2005/0053642 A1 | 3/2005 | Ulbricht et al. |
| 2005/0221072 A1 | 10/2005 | Dubrow et al. |
| 2006/0029808 A1 | 2/2006 | Zhai et al. |
| 2006/0240218 A1 | 10/2006 | Parce |
| 2007/0003705 A1 | 1/2007 | Strauss |
| 2007/0166513 A1 | 7/2007 | Sheng et al. |
| 2007/0225785 A1* | 9/2007 | Park .................. A61L 29/14 607/116 |
| 2008/0015298 A1 | 1/2008 | Xiong et al. |
| 2008/0226694 A1 | 9/2008 | Gelbart et al. |
| 2008/0241512 A1 | 10/2008 | Boris et al. |
| 2009/0011222 A1 | 1/2009 | Xiu et al. |
| 2009/0076430 A1 | 3/2009 | Simpson et al. |
| 2009/0227164 A1 | 9/2009 | Broch-Nielsen et al. |
| 2009/0324308 A1* | 12/2009 | Law .................. G03G 15/2053 399/333 |
| 2009/0326639 A1 | 12/2009 | Edin |
| 2010/0021692 A1 | 1/2010 | Bormashenko et al. |
| 2010/0028604 A1 | 2/2010 | Bhushan et al. |
| 2010/0086604 A1 | 4/2010 | Stellacci et al. |
| 2010/0112286 A1 | 5/2010 | Bahadur et al. |
| 2010/0234945 A1 | 9/2010 | O'Leary |
| 2011/0077172 A1 | 3/2011 | Aizenberg et al. |
| 2011/0223212 A1 | 9/2011 | Taton et al. |

FOREIGN PATENT DOCUMENTS

| | | |
|---|---|---|
| WO | 2011094344 A1 | 8/2011 |
| WO | 2011111083 A2 | 9/2011 |
| WO | 2012097879 A1 | 7/2012 |
| WO | WO-2012097879 A1 * | 7/2012 ............... A61B 5/00 |

OTHER PUBLICATIONS

Ishino, C. et al., "Nucleation scenarios for wetting transition on textured surfaces: The effect of contact angle hysteresis," Europhys. Lett., 76(3) pp. 464-470 (2006).

* cited by examiner

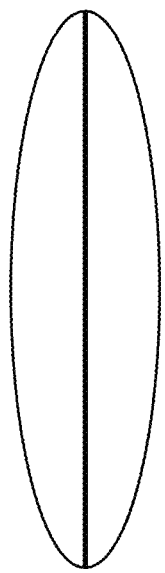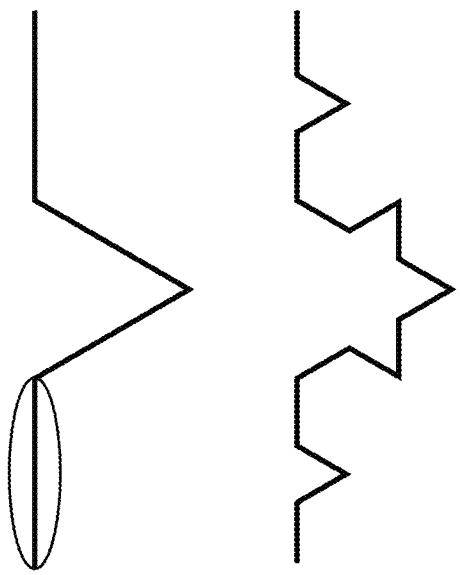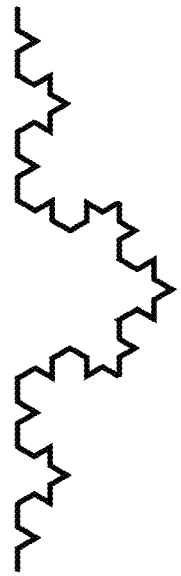
*FIG. 7A*  *FIG. 7B*  *FIG. 7C*  *FIG. 7D*

BIO-SELECTIVE SURFACE TEXTURES

RELATED APPLICATION

This application claims the benefit of priority to U.S. Provisional Application No. 61/589,907, filed on Jan. 24, 2012, the contents of which are hereby incorporated by reference in their entirety.

TECHNICAL FIELD

The present disclosure provides implantable medical devices comprising surface textures on a substrate that, upon implantation in a host tissue, create interfaces with liquids present in the host tissue. The implants in certain embodiments advantageously prevent or reduce undesirable tissue adhesion, bacterial growth and/or biofilm formation while promoting the attachment or ingrowth of desired host tissue.

BACKGROUND

The interaction of a solid textured surface with water in a gaseous environment is described by the Cassie-Baxter model. In this model, air is trapped in the microgrooves of a textured surface and water droplets rest on a compound surface comprising air and the tops of micro-protrusions. The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called superhydrophobic surfaces.

Super hydrophobicity is variously reported as a material exhibiting a contact angle with water that is greater than contact angles achievable with smooth but strongly hydrophobic materials. The consensus for the minimum contact angle for a superhydrophobic substance is 150 degrees.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a small difference between advancing and receding contact angles (i.e., low contact angle hysteresis) presents clinically desirable properties. Water can travel across a surface having low contact angle hysteresis more readily than across a surface having a high contact angle hysteresis, thus the magnitude of the contact angle hysteresis can be equated with the amount of energy needed to move a substance across a surface. In clinical applications, the contact angle relates to the mobility of the implant in situ.

The classic motivation from nature for surface texture research is the lotus leaf, which is superhydrophobic due to a hierarchical structure of convex cell papillae and randomly oriented hydrophobic wax tubules, which have high contact angles and low contact angle hysteresis with water and show strong self-cleaning properties. A lesser known motivation from nature is the red rose petal, with a hierarchical structure of convex cell papillae ornamented with circumferentially arranged and axially directed ridges, which have a moderate contact angle and high angular contact difference.

The contact angle is a measure of the amount of water directly in contact with the implant surface, while the contact angle hysteresis is a measure of the degree to which water is mobile on a surface. The evolutionary motivation for each of these states is quite distinct. In the case of lotus, and botanical leaves generally, minimal contact with water and high water mobility results in preferential adherence of the water to particulate contaminants, which are cleared from the leave as the water runs off. This serves to reduce to the amount of light absorbance by surface contaminants, and increase photosynthetic efficiency. In the case of the rose petal, and botanical petals generally, most pollinators are attracted to high tension water sources which provide ready accessibility without drowning the insect. Thus, high contact angle paired with high contact angle hysteresis is preferred where the evolutionary stimulus is reproduction in botanicals, and high contact angle paired with low contact angle hysteresis is preferred where the evolutionary stimulus is metabolism and growth.

Considering for a moment a single texture scale, when water is placed on a textured surface it can either sit on the peaks of the texture or wick into the valleys. The former is called the Cassie state, and the later the Wenzel state. When the Wenzel state is dominant, both the contact angle and contact angle hysteresis increase as the surface roughness increases. When a roughness factor exceeds a critical level, however, the contact angle continues to increase while the hysteresis starts decreasing. At this point, the dominant wetting behavior changes, due to an increase in the amount of air trapped at the interface between the surface and water droplet.

In the botanical world, such as with the lotus leaf or rose petal discussed above, most textured surfaces occur on substrates that are hydrophobic. However, when a hydrophobic fluid replaces the water, a Cassie state can easily be converted to a Wenzel state. This is not always the case, and depends on the vapor pressure and viscosity of the hydrophobic material and how quickly the air trapped in the surface texture can be dissipated.

It would be advantageous to use microstructured surface textures, such as those found in nature or other microstructured surfaces, in implantable medical devices in order modulate the hydrophobicity of the device, thereby modulating tissue and bacterial adhesion.

BRIEF SUMMARY

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

The methods and embodiments of the disclosure are applicable to absorbable and permanent implantable materials, where absorbable materials are preferred. The materials can be used in implantable medical devices.

One embodiment of the disclosure provides an implantable medical device comprising at least two surface textures on a substrate, wherein upon implantation in a host tissue the surface textures form interfaces with liquids present in the host tissue, wherein a first surface texture traps air between the device and the tissue to form a first interface; and a second surface texture does not trap air between the device and the host tissue to form a second interface; wherein the interfaces have a contact hysteresis angle of at least 5 degrees.

The disclosure further relates to physiologically absorbable, non-fibrogenic, hydrophilic materials that are made relatively hydrophobic during a first time interval by the addition of surface texture. Alternatively, the disclosure relates to physiologically absorbable, generally fibrogenic, hydrophobic materials that are made relatively hydrophilic during a first interval by the addition of surface texture.

The disclosure relates to implantable, absorbable sheets which are hydrophilic, and possibly swell or even dissolve in situ, whereby the addition of a hydrophobic surface texture reduces the rate of absorption or conformal change in situ. Alternatively, the disclosure relates to hydrophobic implantable sheets that do not absorb quickly in the body, which are made to absorb more quickly with the addition of a hydrophilic surface texture.

The disclosure relates to implantable devices comprising surface textures which favor one substance or living structure within a mammalian body over another substance or living structure. For example, a surface filtering effect can be achieved with the devices described herein, wherein a first substance or structure is brought into more intimate contact with the implant than another substance or structure. The intimacy level is characterized by the spatial scale of interactions.

In particular, the disclosure describes a surface filter effect wherein one species characterized by scale or polarity is excluded and another species characterized by scale or polarity is attracted, or both are excluded, or both are attracted, on the same side or on opposite sides of a sheet implant. For example an implant may comprise a side in which bacteria are excluded and a component of tissue is attracted and on the other side bacteria are excluded and a component of tissue is excluded.

The present disclosure further provides implantable materials comprising textures that initially create Cassie and Wenzel states when exposed to an aqueous environment in a mammalian body. In further embodiments, implantable materials comprised of textures that after a period of time create analogs to Wenzel and Cassie states that include a solid hydrophilic phase, a liquid hydrophobic phase, and a liquid hydrophilic phase. In these modified Wenzel and Cassie states, the trapped phase analogous to the classical gaseous phase is the liquid hydrophobic phase. In other embodiments, implantable materials comprised of textures that later replace a gaseous with a liquid hydrophobic phase.

In other embodiments, the disclosure provides implantable, absorbable sheets comprising a hydrophilic substrate that can possibly swell or even dissolve in the host tissue, whereby the addition of a hydrophobic surface texture reduces the rate of absorption or conformal change in the host tissue.

The disclosure further provides implantable absorbable sheets comprising a hydrophobic substrate that does not absorb quickly in a body and that can be made to absorb quickly with the addition of a hydrophilic surface texture.

In particular embodiments of the medical devices disclosed herein, the dominance of Wenzel over Cassie states, or the converse, or their analogues, can evolve as a function of time as the outer surfaces of the device are removed by hydrolysis or enzymatic degradation in the host tissue.

In particular embodiments of the medical devices disclosed herein, a filter effect is created and one species characterized by scale or polarity is excluded and another species characterized by scale or polarity is attracted, or both are excluded, or both are attracted, on the same side or on opposite sides of the implant. For example, a first side excludes a first component of tissue and a second component of tissue is attracted and wherein a second side excludes bacteria and a component of tissue is excluded.

In particular embodiments, the rate of the first surface texture absorbance is chosen to mitigate tissue adhesion and bacterial colonization, especially biofilm formation in a first time interval, and to becomes a smooth, hydrophilic, rapidly absorbing and non-fibrogenic material in a second time interval.

In particular embodiments, accentuation of surface charge and surface energy of the substrate occurs such that water is always bonded to the substrate surface, even though any particular water molecule may have a short residence time on the surface.

In particular embodiments, the surfaces of the implantable medical device are both shielded from protein adhesion and also self-washing due to stochastic attachment/detachment of water molecules from the surface.

In particular embodiments, a folding or rolling effect on bacterial colonies is induced, such that the external biofilm layer encapsulates and excludes the evolving bacterial colony from the surface of the medical device.

BRIEF DESCRIPTION OF THE DRAWINGS

FIGS. 7A-D Example of Kock snowflake surface texture.

DETAILED DESCRIPTION

Figure 1:
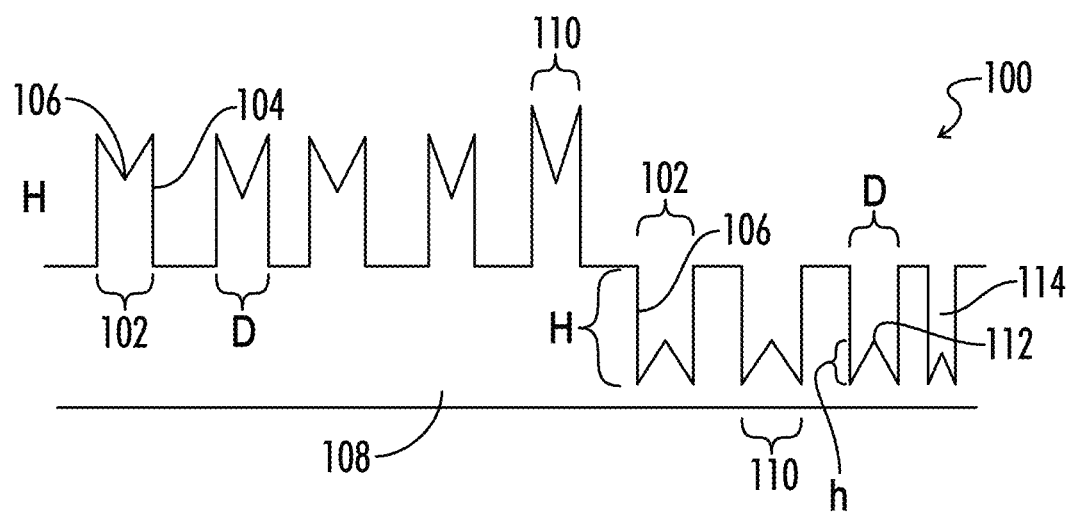
FIG. 1 General view of an implantable prosthetic of the present disclosure possessing a hierarchical surface.

Reference now will be made in detail to the embodiments of the present disclosure, one or more examples of which are set forth herein below. Each example is provided by way of explanation of the materials and implantable medical devices of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure provides an implantable medical device comprising at least two surface textures on a substrate, wherein upon implantation in a host tissue the surface textures form interfaces with liquids present in the host tissue, wherein a first surface texture traps air between the device and the tissue to form a first interface; and a second surface texture does not trap air between the device and the host tissue to form a second interface; wherein the interfaces have a contact hysteresis angle of at least 5 degrees. The medical devices may comprise the surface texture material, or the medical devices may comprise other materials commonly used in the art having the surface texture material disposed thereon. The surface texture refers to a microscale texture or pattern disposed in the substrate material, for example, as described by the methods described herein below. In particular embodiments, the surface texture comprises a hierarchical structure.

In particular embodiments, the contact hysteresis angle ranges from at least 5 degrees to about 90 degrees. In other embodiments, the contact hysteresis angle ranges from at least 5 degrees to about 75 degrees, while in further embodiments, the contact angle hysteresis ranges from about 10 degrees to about 75 degrees.

In another embodiment, after a period of time after implantation, the interfaces comprise: a) a solid hydrophilic phase, b) a liquid hydrophobic phase, and c) a liquid hydrophilic phase. In yet another embodiment, the implantable medical device of claim 1, wherein the trapped air is replaced by a liquid hydrophobic phase after a period of time. For example, the period of time may be about 5 minutes to 12 hours, or more particularly, about 5 minutes to about 6 hours, or about 30 minutes to about 6 hours.

In another embodiment, the surface textures comprise hydrophilic absorbable materials, wherein the hydrophilic absorbable materials are made less hydrophilic by the surface textures, and the surface textures reduce the rate of absorption or conformal change of the medical device in the host tissue. In other embodiments, the surface textures comprise hydrophobic absorbable materials, wherein the hydrophobic absorbable materials are made less hydrophobic by the surface textures, and the surface textures increase a rate of absorption or conformal change of the medical device in the host tissue.

In other embodiments, at least one surface texture comprises absorbable materials, wherein the at least one surface texture is modified by absorption, such that the at least one surface texture becomes more wetting or less wetting as the medical device is absorbed.

In yet further embodiments, the surface textures have a rate of absorbance in the host tissue that mitigates tissue adhesion, bacterial colonization, and/or biofilm formation during a first time interval, and wherein the surface textures become a smooth, hydrophilic, rapidly absorbing and non-fibrogenic material during a second time interval. For example, a first time interval may range from about 5 minutes to about 6 hours, or about 10 minutes to about 6 hours, about 10 minutes to about 3 hours, or about 10 minutes to about 30 minutes, and a second time interval may range from about 30 minutes to about 12 hours, about 30 minutes to about 6 hours, about 1 hour to about 6 hours or about 3 hour to about 6 hours.

In certain embodiments, at least one surface texture comprises a smaller pitch of 10 nanometers to 1 micron, and another surface texture comprises a pitch of 2 microns to 100 microns, wherein the smaller surface texture is disposed on the larger surface texture, such that a hierarchical structure is provided. In some embodiments, the smaller surface textures traps the air, while the larger surface texture does not trap air. In a different embodiment, the larger surface texture traps air and the smaller surface texture does not trap air. The interfaces thus formed depend in part on the pitch size, the pattern of the texture, and/or the substrate material used to prepare the surface texture, as described in more detail hereinbelow. In a particular embodiment, the first interface excludes attachment of a first host derived substance and the second interface promotes attachment of a second host derived substance. For example, the first host derived substance may be a microbe and the second host derived substance may be host cells. In another example, the first host derived substance is a protein and the second host derived substance is host tissue. In another example, the first host derived substance is a host tissue and the second host derived substance is endothelial cells.

In further embodiments, upon implantation in the host tissue, a surface charge of at least one surface texture increases such that water is more strongly bonded to the substrate surface, but not so strongly bonded so as to preclude exchange of water molecules bonded to said substrate surface with surrounding water in the host tissue. For example, a layer of water may adhere to the surface of the device and said water layer reduces the rate of protein molecule adsorption to said textured surface, relative to a device comprised of said substrate without surface texture. Furthermore, a layer of water may adhere to the surface textures of the device, such that the water layer reduces a rate of protein molecule adsorption to the textured surface, relative to a device without the surface textures.

In particular embodiments, wherein the substrate is porous. For example, the substrate may comprise three dimensionally interconnected pores.

In some embodiments, the first surface texture forms a Cassie state when implanted in host tissue and the second surface texture forms a Wenzel state when implanted in host tissue. In further embodiments, at least one of the surface textures comprises fibers embedded in and protruding from the substrate, and the fibers are bifurcated at least once on at least one spatial scale different from a pitch of other surface textures of the device. In yet a another embodiment, at least one of said surface textures is comprised of fibers embedded at both ends in said substrate and said fiber and protrude from said substrate, and said fibers form loops with at least one diameter different from the pitch of other surface textures of the medical device.

In certain embodiments, the surface textures may comprise or be similar to certain mathematical fractal shapes. For example, in some embodiments, at least one surface texture comprises a Koch snowflake pattern, a Sierpinski gasket pattern, Apollonian gasket pattern, or a diffusion limited aggregation pattern.

In certain embodiments, the aforementioned implantable medical devices comprises two sides, such as a sheet structure, wherein the two sides have different surface texture patterns. In one embodiment, the surface textures form interfaces with liquids present in host tissue, wherein at least one surface texture traps air between the device and tissue and at least one other surface texture does not trap air between the device and tissue, and wherein the resulting interfaces generate a contact hysteresis angle of at least 5 degrees on one side (for example, the contact angle hysteresis can be at least 5 degrees to about 90 degrees, at least 5 degrees to about 75 degrees, or about 10 degrees to about 75 degrees), and less than 5 degrees (for example, an angle of about 0.1 to less than 5 degrees, or more particular, about 0.5 to less than 5 degrees, or more particularly, about 0.5 to about 3 degrees) on the other side of the device.

It should be understood that the structures of the present disclosure are not intended to be strictly superhydrophobic, and should not be limited on that basis. For example, a typically hydrophilic material can be rendered more hydrophobic by the addition of surface structure, but such addition does not require the surface to be superhydrophobic, by the usual definitions.

While not being bound by any particular theory, the implantable medical devices can be further understood as explained by the principles described below. The contact angle for a water droplet on a smooth surface is dictated by the electronic structure of the molecules comprising the smooth surface. The highest contact angle due to electronic structure alone is approximately 120 degrees. High surface energy substances tend to reduce the contact angle with a polar substance such as water. When water spreads over a solid surface it increases its own surface energy at the expense of lowering the surface energy of the solid. The net result is a reduction of the total surface energy of the solid and water combination relative to if they were apart.

Water, when not in contact with a solid, is in its lowest energy state when it is in the shape of a sphere. Lower surface area equates with lower surface energy, and for a given volume a sphere corresponds to the shape with minimum surface area. A solid with low surface energy will not cause water to spread across its surface (increase its surface area) because the increase in energy needed to spread the water across the solid exceeds the available energy at the solid surface. Molecules comprised of fluorine and carbon atoms typically have some of the lowest surface energies, for example, $CF_3$ groups have a low surface energy of 6.7 mJ/m2. Surfaces with lower surface energy are defined as superhydrophobic, with a water contact angle greater than 150 degrees. To achieve these high contact angles the solid surface must be textured.

Surface energy quantifies the disruption of intermolecular bonds that occur when a surface is created. In the physics of solids, surfaces must be intrinsically less energetically favorable than the bulk of a material, otherwise there would be a driving force for surfaces to be created, removing the bulk of the material. For bioabsorbable materials, the bulk energy is relatively high compared to the surface energy, and the energy of the surface dissolved is lower than the surface energy. Thus there is a driving force for the bioabsorbable material to be absorbed. These materials must have a relatively high surface energy to promote interaction with water in the body. On the other hand, a high surface energy substance promotes protein and cell attachment, resulting in what is known as a foreign body response and microbial colonization. A high foreign body response results in inflammation and fibrosis. Accordingly, the present disclosure employs hydrophilic materials with high surface energy that are made more hydrophobic (but typically not superhydrophobic) and less prone to bacterial colonization by employing hierarchical surface texture.

The mechanisms responsible for the effect of surface roughness were addressed by Wenzel and later by Cassie and Baxter. The interaction of water with a smooth surface is characterized by Young's angle θy. The wettability of an ideal flat solid is quantified by the Young equation, $$\cos θy = (γs\text{-}g - γl\text{-}s)/γl\text{-}g,$$

where γs-g, γl-s, and γl-g represent the interfacial tensions of solid-gas, s-g, liquid-solid l-s, and liquid-gas, l-g interfaces, respectively.

For a textured surface, there are two water contact states corresponding first to water filling the interstitial sites (Wenzel) and second gas trapped in the interstitial sites by a layer of water (Cassie). For textured surfaces with a multiplicity of surface texture spatial scales it is possible for the larger scaled texture to form contact with water in the Wenzel state and for smaller scale texture to form contact with water in the Cassie state. This mixed water contact surface state is commonly called the Cassie wettable state.

A characterization of the Wenzel state can be obtained by generalizing the Young equation. To do so, we define an apparent contact angle θa, and relate θa to θy by $$\cos θa, w = r \cos θy,$$

where r is termed the "roughness factor" and is defined as the ratio of the actual area of contact on a rough surface to the projected area of contact in the contact plane.

A characterization of the Cassie state can be obtained by generalizing the Young equation. To do so, we relate the apparent contact angle θa to θy the apparent contact angle in the Cassie state is given by $$\cos θa, c = rf \cos θy + f - 1,$$

where f represents the fraction of the projected area that is wetted by the liquid.

These equations relate surface energy to the geometry of solid/liquid interface in equilibrium. In the implant environment, nothing is static, and the Brownian motion of different chemical constituents is responsible for repeated association and disassociation with a surface. The surface may itself be changing where a portion or all of a surface is absorbable.

When the energy to form a liquid/solid interface is different from the energy to disassociate a liquid/solid interface, then their contact angles are different, and this difference is called contact angle hysteresis. Contact angle hysteresis is defined here as the difference between association and disassociation contact angles. This hysteresis occurs due to the wide range of "metastable" states which can be observed as the liquid surface tension interacts with the surface of a solid at the phase interface.

The present disclosure discloses an implant that is absorbable, resistant to bacterial colonization, and is reversibly adhesive to tissue. The adhesive aspect of a Cassie wettable state is one in which the energy to associate water with a surface is less than the energy required to disassociate that interface, even in cases where the overall surface energy is quite low (high contact angle). The contact angle hysteresis is achieved by allowing one scale of roughness to be Wenzel and another scale of roughness to be Cassie. This condition is known as the "petal effect".

In contra-distinction, when all scales of roughness are Cassie (non-wetting) and when the material is hydrophobic then the material is typically superhydrophobic. In this case, formation of a liquid/solid interface requires relatively more external energy than for the Cassie wettable state, and the association of liquid/solid contact and the disassociation of liquid/solid contact are approximately equally disfavored (low contact angle hysteresis). This results in the "lotus effect" where liquid/solid interface comprises low surface area forms and is easily disassociated. Superhydrophobic surfaces are not adhesive to tissue.

Thus, the lotus (Cassie) and petal effects (Cassie wettable) can be characterized by the following equation:

$$\cos \theta a = Q1 \cos \theta 1 \pm Q2 \cos \theta 2$$

which describes the effect of surface heterogeneity on the contact angle. In this equation, θa, the apparent angle, is the weighted average of the contact angles of two roughness scales of the surface. This equation can be generalized to any number of scale hierarchies. The quantities Q1 and Q2 represent the fraction of the surface covered by liquid/solid interface for each of the roughness scales characterized by contact angles θ1 and θ2. When θ1−θ2 is large (contact angle hysteresis), θa characterizes a petal effect and is generally adhesive. When θ1−θ2 is small, θa characterizes a lotus effect and is generally repulsive.

In view of these equations, we derive for the first time, an equation for describing a wettable Cassie state. For the petal state one of the θ is θac (Cassie) and the other θ is θaw (Wenzel) and for the lotus state both of the θ are θac (Cassie). For example, setting θ1=θac and θ2=θaw, then the complete equation is $$\cos \theta a = Q1 \cos \theta ac \pm Q2 \cos \theta aw = Q1(rf \cos qy + f - 1)$$
$$\pm Q2(r \cos qy)$$

Now, noting that the contact angle is determined by both a) the hydrophobicity/hydrophilicity (surface electronic structure) of the substance comprising the surface and b) its texture. The above equation assumes the solid surface is comprised of a single substance and represents only the hierarchical structure of the surface texture.

Now consider a solid surface with both hierarchical surface texture and hierarchical changes in surface hydrophobicity. Thus the apparent angle θac or θaw is a function of both structure scale and surface electronic structure. Thus spatial structure and electronic structure are interchangeable when $$\theta ac(\text{spatial}) = \theta ac(\text{electronic})$$

$$\theta aw(\text{spatial}) = \theta aw(\text{electronic})$$

θa (spatial) is dependent solely on the Young equation, accordingly, for the first time, the most general equation for the apparent contact angles is $$\cos \theta a = \Sigma_{i=1,n}[Q_i(r_i f_i \cos \theta y_i + f_i - 1)] \pm \Sigma_{i=n+1,n} Q_i(r_i \cos \theta y_i).$$

This equation is critical to the design of the implants of the present disclosure.

In the implant environment the surface of a solid is modified by relatively amphiphilic aqueous constituents. The implant/tissue interfacial tension can be modified by amphiphilic constituent addition caused by the adsorption of amphiphilic proteins onto the implant and can be described by the Gibbs adsorption equation, which relates the surface excess concentration Γs to the interfacial tension γ by $$\Gamma s = -(1/k_B T)(d\gamma/d \ln c_p).$$

Where $c_p$ is the surface protein concentration, T is temperature and $k_B$ is the Boltzmann constant.

When $c_p$ exceeds a critical density the protein monolayer of l-g or l-s interface becomes saturated, because both γl-g and γl-s are unchanged. In vivo constituents are unable to reduce γl-s further to satisfy the condition, γl-s<γs-g, at saturation and thus the surface remains in a hydrophobic range. Since the l-s interface is saturated before the l-g interface is, contact angle reduction for in vivo constituents is controlled by surface tension (γl-g). Contact angle hysteresis is generally increased with the surface protein concentration. Nonetheless, like the association contact angle, contact angle hysteresis evolves to be independent of surface protein concentration as $c_p$ approaches the critical protein density.

Thus we achieve an equilibrium protein concentration where the probability of protein adhesion equals the probability of protein release. The implant surface becomes self-washing, despite the association of adhesive protein constituents to the implant surface. The temporal instability of the bonding of these constituent proteins to the implant surface renders the implant incapable of supporting bacterial colonization while providing enough protein adhesion to direct tissue growth through the implant and releasing the tissue ingrowth to the interstitial spaces of the implant if the implant is porous, and release tissue from adhesion if the implant is non-porous.

The present disclosure is directed to adapting the surface texture effects resulting in Wenzel and Cassie states under implant conditions, in particular, the adaptation of petal and lotus effects, and in particular wettable Cassie and dry Wenzel states, to an implant environment. Therefore, except where polymers are used which actively entrap a gas state on an implant surface, such as fluorocarbons, a gas state cannot be relied upon to create the desired in vivo states. Biological fluids are far from homogeneous, and comprise discrete hydrophilic and hydrophobic components, suspended macromolecules, and several size scales of sub-cellular, cellular, and tissue structures.

The present disclosure teaches methods and devices which use surface texture induced states to organize constituents of a liquid biologic medium. These methods comprise the use of scale hierarchical surface geometry, scale hierarchical surface regions, hydrophobicity/hydrophilicity, and scale hierarchical regions of gas phase adhesion.

According to this disclosure, it is proposed to use spatially hierarchical surfaces as regards their geometry, that is ones that are linearly and fractally arranged in a scale ranging from tens of micrometers down to several nanometers. Considering that only the outermost portions of individual hierarchic levels are wetted (contact water), such structures should be characterized by a very small surface of effective contact between the solid and bodily aqueous fluids, even below 1% of the coating surface.

It should be understood that at any level, the percentage of water association is critical, and not the absolute value of the amount of water association, such that at various fine scales the amount of water interaction with the surface may be very small but the clinical consequence could be great relative to the percentage of water at that particular scale which is interacting with the surface structure. Conversely, in the non-contact area and where air is initially trapped, lipid constituents are preferentially attracted, particularly tissue constituents, which replace the regions occupied by air.

In at least one embodiment of the present disclosure produces a dramatic reduction in surface area available for microbial attachment and foreign body response. When lipid films attach, the result is that the film acts as a low energy surface which is energetically disfavored for protein attachment and microbial colonization. In particular, one side of an implantable sheet can possess a Cassie wettable state for localizing the implant to tissue, and the other side can possess a pure Cassie state for resisting tissue adhesions.

In another embodiment, the substrate material may have on one side a layer which is relatively rapidly absorbable and hydrophilic and on the other side is a layer which is relatively slowly absorbable and hydrophobic such that the texture on the two sides produce a Cassie wettable state on one side and a superhydrophobic pure Cassie state on the other side.

In another embodiment, the tissue adhesive surfaces of the present disclosure bind to tissue spontaneously in the presence of water. Without wishing to be bound by theory, it has been reported that hydrophobic bonding is based on very-long-range attractive forces. These forces are due to lipid separation resulting in a phase-like transition in bodily fluid present at an implant site. This change is characterized by a sudden, strong attractive force and by the formation of lipid bridges. In contradistinction, implantables with long-range attractive forces are described.

In another embodiment of the present disclosure, such attractive forces between a textured implant surface and tissue are employed to (reversibly) bind an implant to a surgical site.

In another embodiment, the surface texture of an implant may be chosen to induce a filtering effect, wherein certain molecules, cellular structures, or tissue components are attracted while others are repelled, and this attractive/repulsive effect varies across different surface texture spatial scales. This filter effect can be employed to produce local separation of normally homogenous in vivo constituents wherein the separation occurs at different levels of the implant surface.

The surfaces of the present disclosure, be they pure Cassie, pure Wenzel or Cassie wettable, or analogues, possess low surface energy, and the affinity of bacteria to bind to tissue or themselves is energetically favored over binding to the implant surface. More particularly, if microbes should colonize the implant surface the spreading of a protective biofilm is energetically disfavored. Consequently, an evolving biofilm would tend to take on a spherical shape, which turns the biofilm surface to encapsulate the bacterial colony and decrease the contact area with the implant surface.

In another embodiment, the implant produces a folding or rolling effect on bacterial colonies, such that the external biofilm layer encapsulates and excludes the evolving bacterial colony.

The present patent introduces the concept of using structured surfaces consisting of non-communicating (closed cell) roughness elements to prevent the transition of a water droplet from the Cassie to the Wenzel state. The resistance to the Cassie-Wenzel transition can be further increased by utilizing surfaces with nanostructured (instead of microstructured) non-communicating elements, since the resistance is inversely related to the dimension of the roughness element.

One aspect of some embodiments of the present disclosure are dimpled or impressed surfaces that offer increased resistance to droplet transition to the Wenzel state compared to a dimensionally equivalent pillared surface. The presence of air trapped inside the non-communicating craters and the resistance to fluid motion offered by the crater boundaries and corners are two sources of this increased resistance to the transition to a Wenzel state and enhance adhesiveness in vivo.

The impressed or concave textured surfaces of the present disclosure preferably possess a fractal structure or hierarchic structure wherein the forms of the first hierarchic level are located next to the coating substrate and the forms of each successive level are located on the surface of forms of the previous hierarchic level and the shape of forms of higher hierarchic levels reiterate the shapes of lower hierarchical levels and the structure contains forms of at least two hierarchical impressions.

The substrate of the biocompatible implants of the present disclosure are polymeric materials with possibly one or more nano-scale textures with dimensional spacing of 10 to several thousand nanometers and at least one micro-scale texture with dimensional spacing of 10 to about 100 microns. The polymeric material is preferably heat meltable without decomposition or soluble in a solvent, so that the texture may be embossed in the melt state or cast in the solvent state.

Generally, texture refers to topographical and porosity elements, including elevations and depressions on the surface and mass distribution in the volume of a polymeric surface and of the layer comprising the surface. The polymeric layer may be made of multiple polymer types, and may contain other material being embedded in the polymer and contributing to the topography, For example, non-polymeric or polymeric fibers or particulate may be dispersed on the surface of the polymer substrate, which matrix by itself may comprise more phases or components. In particular, components with absorption rates in a mammalian body slower than the bulk polymer such that a desired texture is preserved for an extended period during the dissolution process. Alternatively, these slower absorbing elements are embedded in the polymeric substrate homogeneously or on several levels such that several different topologies are presented during the course of dissolution.

The textured implants of this disclosure can have many variants and combinations that are specified as follows: The implant can have a homogenous bulk composition wherein grooves, ridges, protuberances or indentations are located, on at least two spatial scales, on the surface of implant. The implant can have a porous substrate with three dimensionally interconnected pores. The implant can have a solid substrate with interconnected channels or non-interconnected indentations on the implant surface. The implant can have a first small scale texture embossed on a second larger scale structure, or a hierarchical arrangement of such scales. The implant can have a first small scale texture that is concave and non-communicating embossed on a second larger scale structure that is convex and communicating, or a hierarchical arrangement of such structures. The implant can have a first small scale texture that is Cassie embossed on a second larger scale structure that is Wenzel, or the reverse. The implant can have grooves or ridges deployed in a step-like contour on larger scale convex protuberances. The implant can have a semi-open structure wherein hierarchical texture is located on cross elements, such that the semi-open structure itself comprises a texture. The implant can have fibers imbedded and protruding from the polymer substrate, said fibers can be bifurcated on a number of spatial scales in the manner of the fibers disposed on a Gecko foot. The implant can have fibers attached by both ends in the polymeric substrate, thus determining loops, the radius of said loops of at least two length scales. The implant of any combination of the above.

A scale of interaction is defined by the surface texture of the implantable device, and is typically hierarchical, and characterized by at least two spatial scales, one on the order of micrometers (microns) and another on the order of nanometers. The surface texture may induce one state with a large difference between preceding and receding contact angles (contact angle hysteresis), or alternatively another state with a small contact angle hysteresis. States of interest, or their in situ analogues, are known respectively as Wenzel and Cassie states. Each of the hierarchical spatial scales may induce separately a Wenzel or Cassie state, such that combinations are possible on a multiplicity of spatial scales.

These states are three phase phenomena, and classically consist of solid, liquid and gaseous contacts mediated by the dimensionality of the surface texture. Since the gaseous component eventually dissipates in vivo by a combination of liquid evaporation into the gaseous domain and gas dissolution into the liquid domain, the Cassie state eventually evolves into the Wenzel state in living tissue.

The present disclosure relates to implantable materials comprised of textures that initially create Cassie and Wenzel states when exposed to an aqueous environment in a mammalian body. These states evolve in situ, and their evolution analogues differ from typical Wenzel and Cassie states in that they involve a solid hydrophilic phase, a liquid hydrophobic phase, and a liquid hydrophilic phase or a solid hydrophobic phase, a liquid hydrophilic phase, and a liquid hydrophobic phase. In these modified Wenzel and Cassie states, the trapped phase analogous to the classical gaseous phase is the liquid hydrophobic phase. Alternatively, a trapped gaseous phase is preferentially replaced by a liquid hydrophobic phase.

The Cassie and Wenzel phenomena, occur when three phases are in contact with one another. In the body, the respective states lead to the formation and retention on an implant of a liquid hydrophobic film in the Cassie state and retention of tissue (containing lipids) in the Wenzel state. These are clinically useful attributes.

In the Cassie state the implant is resistant to cellular and bacterial adhesion. In the Wenzel state the implant is reversibly adherent to tissue. In hybrid Cassie-Wenzel states, where one texture scale is Wenzel and the other is Cassie, the implant can be both localizing to a tissue surface and resistant to bacterial colonization and tissue adhesions. Opposite sides of an implant may be biased toward tissue localization on one side and resistance to tissue adhesion on the other side, while both sides may exhibit both properties to greater or lesser extent. The dominance of Wenzel over Cassie, or the converse, can evolve as a function of time as the outer surfaces are removed by hydrolysis or enzymatic degradation. In particular cases, the spatial frequency of the various structure scales may be modulated at various implant depths, presenting a changing spatial frequency as the surface layers of the implant are removed.

Alternatively, the surface texture may be chosen to present to tissue on one side of the implant a high surface area relative to a second side with low surface area.

Alternatively, the surface texture may be chosen to modulate the hydrophobicity of a single implant material to control water absorbance, biodegradation, and drug elution differentially relative to regions or whole sides of the implant.

Finally, the rate of surface texture absorbance is chosen to mitigate tissue adhesion and bacterial colonization, especially biofilm formation in a first time interval and to reduce to a smooth, hydrophilic, rapidly absorbing and non-fibrogenic material in a second time interval.

Low contact angle hysteresis, and generally superhydrophobic surfaces are desired where interaction with biological constituents such as cells, platelet, microbes is to be minimized. In biological systems, one must consider the constituents in the living environment which will associate with the implant surface, and create the critical hierarchical structure of surface roughness needed to establish a Cassie, Wenzel, or combined state long-term in vivo.

When multiple texture scales are employed, some can be Wenzel and others Cassie. Of the two states, the Wenzel state has the lower contact angle, higher contact angle hysteresis and lower mobility. In mixed Wenzel-Cassie states it is possible to have high contact angle and high contact angle hysteresis. However, the hydrophobicity of a textured solid relative to the interacting liquid is very important.

Water possesses a dipole structure which makes it attractive to any other substance that is charged. Implantable molecules with a charge surplus localized at a specific location on the molecule renders that molecule hydrophilic. In the case of polymers, the charges can associate, and the bulk substance and possess a macroscopic charge. And in such macroscopic assemblages, such materials are strongly water attractive. And when those macroscopic charge localities are associated with surface texture, than a substance becomes super hydrophilic. The term super hydrophilic has various meanings in the literature, and in many cases simply refers to the rendering of a substance more hydrophilic, or a decrease in contact angle relative to a flat surface of the same substance. Here, it is meant the accentuation of surface charge and surface energy such that water is always bonded to the substrate surface, even though any particular water molecule may have a short residence time on the polymer surface.

This has a clinical advantage in that the implant surface is both shielded from protein adhesion and also is self-washing due to the stochastic attachment/detachment of water molecules from the surface.

In the botanical world, most textured surfaces occur on substrates that are hydrophobic. However, when a hydrophobic fluid replaces the water, a Cassie state can easily be converted to a Wenzel state. This is not always the case, and depends on the vapor pressure and viscosity of the hydrophobic material and how quickly the air trapped in the surface texture can be dissipated.

Gas in living tissue is not compatible with living cells, gas surrounding an implant effectively shields the implant from cellular attachment, and in most cases blocks a foreign body response by blocking the adsorption of signaling proteins. Typically, for a chemically inert material, if cells cannot deposit protein on an implant to mark it as a foreign body the body does not react to the implant. This results in low inflammation, low fibrosis and minimal encapsulation. In this case, fibrosis is largely due to surgical disruption of tissue and mechanical disruption of tissue subsequent to closure. Consequently, to maintain a benign implant condition, the implant must be inert, non-adhesive to cellular protein deposition, and be relatively well localized so that differential motion between implant and tissue does not occur.

A hydrophobic substance is a material with low surface energy. Cells attach to surfaces by reducing the surface energy of a material. High surface energy of a material causes cells to stick to a foreign body. On the other hand, a higher surface energy energetically favors water association over protein association. Thus, maximally biocompatible substances tend to be those that are either superhydrophobic or super hydrophilic. Intermediate or even amphiphilic conditions are more typical in vivo, and cellular mechanism have evolved to identify, and eliminate foreign bodies with such properties, resulting in an undesirable foreign body response.

The magnitude of the surface energy reduction is proportional to the magnitude of the adhesive strength between foreign body and deposited protein and associated cell. Typically when cells or bacteria colonize a foreign body, they reduce its surface energy and make it more hydrophobic. This is again an evolutionary tactic, rendering the surface less energetically favorable to other organisms to colonize. Consequently, a low surface energy material provides little "excess" energy to provide strong cellular attachment. However, most hydrophobic materials, for example polytetrafluoroethylene (PTFE), are within the range where the hydrophobic ends of proteins favorably associated with the material, primarily by a lower energy state achieved by leaving a primarily high tension polar environment, such as is typical in situ. By association, the protein changes shape, it may or may not be bound to the foreign body surface, but once it has changed shape it in turn becomes a foreign body, signaling a cascade of responses, chief among them the release of reactive oxygen species, which then can significantly change the charge structure of the implant surface.

By this mechanism proteins are strongly denatured by hydrophobic surfaces. This is because proteins typically carry a charge that relates to its conformal state. Once a protein is denatured, it folds, and is seen as foreign, even though it may be only weakly attached to the foreign body. This can precipitate a sequence of cellular assaults that include macrophages, giant cells, histiocytes and any of the mononuclear phagocyte system, which begin to charge the foreign surface, preparing it for adhesion and encapsulation. If the implant surface is absorbable, the remodeling of the implant surface results in a prolonged attack by oxidizing species and resulting dense fibrosis.

Micro-layers of gas are ideal insulators from a foreign body response because from an evolutionary perspective, gas is almost never in the body and thus cellular mechanisms to ostracize it were never developed. This is primarily due to the fact that gas does not remain long in the gas phase in the body, and readily absorbs into fluids or is metabolized. Important in maintaining the Cassie-like state, is the replacement of gas by a similarly electronically structured constituent.

A particularly stable fluid readily found in the body is lipids. Lipids are moderately hydrophobic and present an ever-changing surface, so protein attachment is inhibited. Lipids also do not denature protein, since lipids are commonly found in the body, especially if such lipids are recruited from the body's own cellular environment. Unlike water, which is another stable fluid readily found in the body, lipids do not allow for the conductance of cells to the underlying implant surface.

One reason why many synthetic hydrophobic materials are highly fibrogenic is that they are both hydrophobic and lipophobic, and thus never establish a protective outer layer. An example of material that is both hydro- and lipophobic is fluorine polymer, for example, PTFE. PTFE is a substance with properties opposite to those of diamond—a highly hydrophobic material that is wetted by fats and is lipophilic. This is why pyrolytic carbon was for a long time pursued as the ideal implant material.

It is known from medical experiments that for contact angles of 150 degrees or less there are no benefits regarding reduction of microbial adherence over a regular hydrophobic material such as fluorocarbons having contact angles of around 120 degrees. By employing a lipid layer rather than a gaseous layer, recognizing its screening benefits, even moderately hydrophobic surfaces are made less microbial conductive.

In order to render an implant compatible with a lipid layer, the hydrophobicity of most absorbable implants must be increased. This presents a conundrum, since a hydrophobic surface will strongly denature proteins. By texturizing an absorbable implant, the amount of surface area of the implant exposed to the in vivo environment is dramatically reduced, and the hydrophobicity is increased to a level to be compatible with lipid layer formation, without inducing protein denaturation at the molecular scale. By choosing a suitable surface texture the small portion of the implant that is directly exposed to the cellular environment is basically hydrophilic and does not illicit a foreign body response through molecular sized interactions.

Hydrophobic surfaces may be created by processing of an existing hydrophilic surface. Typical methods of converting material surfaces to become superhydrophobic include, for example: 1) Etching the existing surface to create specific nano-patterns (patterns which are in the nanometer size range), and subsequently coating the surface with a hydrophobic coating. 2) Roughening the substrate surface using techniques known in the art, and functionalizing the resulting surface by applying a hydrophobic coating. 3) Growing a rough (or porous) film from solutions containing nano-particles or polymers in a way which creates a rough and hydrophobic surface on the material. 5) Vapor deposition of carbon nano-rods on a substrate. 6) Lithography of a silicon substrate, or laser ablation of a polymeric substrate. and 7) Electro-spun fibers deposited on a substrate.

In describing the hierarchical structures of the present disclosure, "protuberance" refers to any higher structure on a macroscopically planar surface and "depression" refers to any lower structure on a macroscopically planar surface. Generally, protuberances and depressions are paired with respect to a specific spatial scale, and reported dimensions thereof are made pair-wise. For example, when a protuberance is reported to be 100 microns in height, that dimension is measured with respect to a near-by depression. In engineering parlance, the measurement is made peak to trough. Lateral measurements are typically made peak to peak or trough to trough, and are referred to as the pitch.

Referring to FIG. 1, generally an implantable prosthetic 100 of the present disclosure possesses a hierarchical surface comprised of a micro-scale structure 102 with a plurality of protuberances 104 and depressions 106 disposed in a geometric pattern on at least one surface of a substrate 108, and a nano-scale structure 110 disposed on at least one surface of the micro-level structure 102. The nano-scale structure 110 is similarly comprised of protuberances 112 and depressions 114.

The micro-scale protuberances 104 should be high enough so that a water drop does not touch the micro-scale depressions between adjacent protuberances 104. In the embodiment of FIG. 1, the micro-scale protuberances 104 may comprise a height H of between about 1 to about 100 microns and a diameter D of between about 1 to about 50 microns, wherein the fraction of the surface area of the substrate 108 covered by the protuberances 104 may range from between about 0.1 to about 0.9. The nano-scale protuberances 112 may comprise a height h of between 1 nanometer to about 1 micron and a diameter d of between 1 nanometer to about 0.5 microns, wherein the fraction of the surface area of the substrate 108 covered by the protuberances 112 may range from between about 0.1 to about 0.9. The nano-scale structure 110 may be disposed primarily on the micro-scale protuberances 104, or alternatively primarily on the micro-scale depressions 106, or primarily uniformly across micro-scale structure 110.

The pitch P between adjacent micro-scale protuberances 104 or depressions 106 may range from between about 1 and about 500 microns. The pitch p between adjacent nano-scale protuberances 112 or depressions 114 may range from between 1 nanometer and about 1 micron.

The arrangement of hierarchical structures may be geometric or describable generally with a mathematical equation. Alternatively, the hierarchical structures may be randomly disposed, possibly with varying pitch, which is more typical of natural structures. The arrangement of hierarchical structure can generally be described by a fractal dimension, F. A fractal dimension is a statistical quantity that gives an indication of how completely a collection of structures appears to fill space, in the present case a plane, as one examines that structure on a multiplicity of spatial scales. For example, a fractal dimension of 1 describes a pure geometric line and a fractal dimension of 2 describes a plane, and so on. Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that a synthetic structure of the present disclosure has greater utility when interacting with a natural surface such as tissue. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. On the other hand, a Fourier decomposition of such structures would provide a fractal-like dimension. For example, a sharp-edged structure would require a greater number of sinusoidal waveforms to describe such a structure in superposition. This corner roundness can be characterized by a radius (R,r), and generally may be different in a direction x relative to a direction y in the plane of the implant.

Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The degree of communication or connectedness c or C (nano-scale or micro-scale, respectively) can be quantified by the ratio of the spatial extent in one direction, for example Dx, and the pitch in an orthogonal direction, for example Py. Accordingly, $Cx=Dx/Py$ and $cx=dx/py$. Furthermore, the communication can vary across the surface of the substrate. The communication may range from 1 to about 1000, more particularly the communication may extend over the entire surface of the substrate.

Figure 2A:
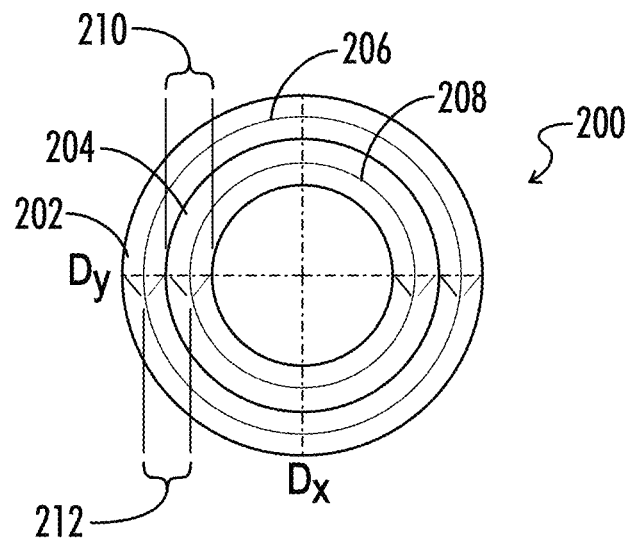
FIG. 2a. Schematic of maximum communication structure C=1.
Figure 2B:
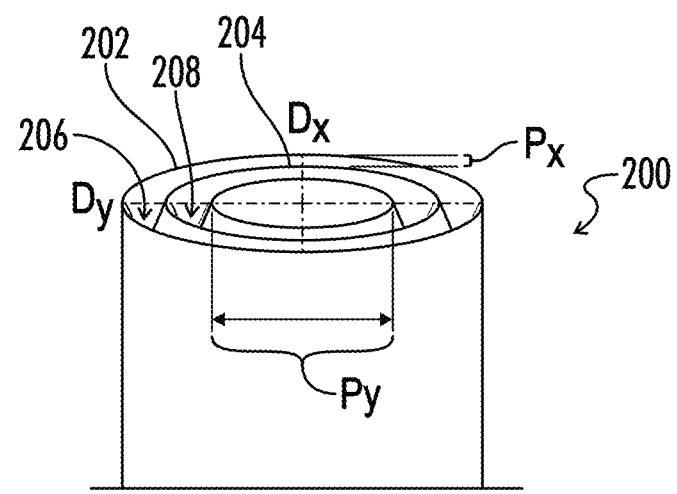
FIG. 2b. Schematic of communication structure C=0.25.
Figure 2C:
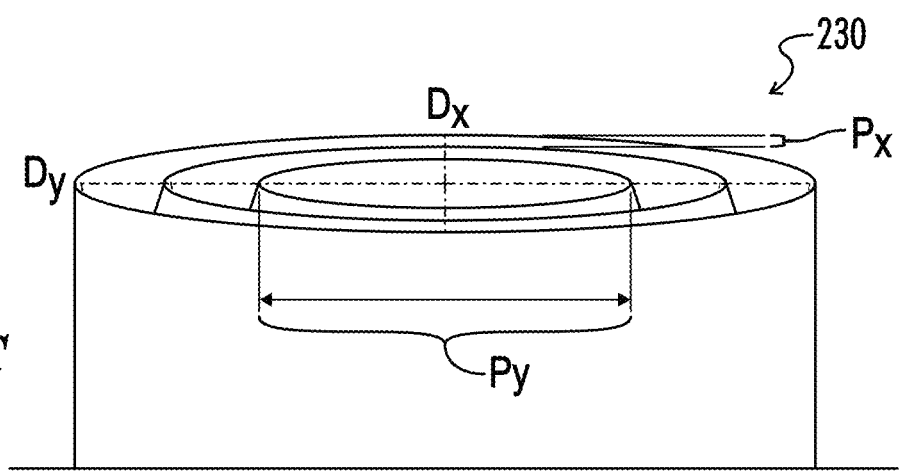
FIG. 2c. Schematic of minimum communication structure C→0.

Referring to FIGS. 2a-c, in FIG. 2a a concentric circular structure 200 is comprised of a first protuberance 202, a second protuberance 204 a first valley 206 and a second valley 208 and is characterized by Dx, Dy, Px, Py. Note for non-varying pitch, the pitch is the same whether measured peak to peak 210 or trough to trough 212. Due to the circular structure, $Dx=Dy$, $Px=Py$ and $D=P$, which gives $Cx=Cy=1$.

Now referring to FIG. 2b, wherein the structure is elliptical 230. In this instance $Dx<Dy$ and $Px<Py$. Let $4Dx=Dy$, $4Px=Py$, and $Dx=Px$, then $Cx=0.25$ Now referring to FIG. 2c, wherein the structure is more elliptical 240. In this instance $Dx<Dy$ and $Px<Py$. Let $100Dx=Dy$, $100Px=Py$, and $Dy=Py$, then $Cx=1/100=0.01$. In the limit where the valleys become parallel the communication $Cx \to 0$.

Accordingly, structures of low communication can be constructed for both depressions and protuberances where reference to a flat, non-textured level is made. For example, a texture may be impressed into a flat planar surface wherein some of these textures are protuberances and other textures are depressions, separated by regions of flat planar surface. Structures can be created wherein the depressions possess a high communication ratio and the protuberances possess a low communication ratio, and conversely.

These structures are constructed with the purpose of creating Wenzel and Cassie states, on a multiplicity of scales, when the prosthetic of the present disclosure is implanted. It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure. Similarly, the Wenzel state can be discouraged by the use of curving communications between structures as opposed to straight line communication. In most cases, higher hydrophobicity equates with lower propensity for a Wenzel transition.

The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples; triangular, rectangular, pentagonal, or hexagonal shapes, regular or irregular; and further polygonal shapes defined generally by straight line segments). A second feature of smaller size and different hierarchical order is then superimposed on the depression wall of the first pattern. The method employed in creating such a structure may involve first emboss a nano-structure and then secondarily emboss a micro-structure.

Alternatively, electronic structure of the substrate may be hydrophobic. Hydrophobic substances suitable for implantation include polyesters made from aliphatic or aromatic dicarboxylic acids and aliphatic and/or aromatic diols, e.g.: polyesters synthesized from aliphatic dialcohols having 2 to 18 carbon atoms, e.g., propanediol, butanediol, hexanediol, and dicarboxylic acids having 3 to 18 carbon atoms, such as adipic acid and decanedicarboxylic acid; polyesters synthesized from bisphenol A and the above mentioned dicarboxylic acids having 3 to 18 carbon atoms; and polyesters synthesized from terephthalic acid, aliphatic dialcohols having 2 to 18 carbon atoms, and dicarboxylic acids having from 3 to 18 carbon atoms.

The polyesters may optionally be terminated by long-chain monoalcohols having 4 to 24 carbon atoms, such as 2-ethyl hexanol or octadecanol. Furthermore, the polyesters may be terminated by long-chain monocarboxylic acids having 4 to 24 carbon atoms, such as stearic acid. In most cases, hydrophobicity is reduced by the presence of polar pendant groups, such as hydroxyls.

Alternatively, polymers containing urethane (carbamate) or urea links or combinations of these can be made hydrophobic by varying the number of these links relative to the molecular weight of the amorphous phase backbone, as well as varying the hydrophobicity of the backbone. Typically, such polymers are formed by combining diisocyanates with alcohols and/or amines. For example, combining toluene diisocyanate with a diol and a diamine under polymerizing conditions provides a polyurethane/polyurea composition having both urethane linkages and urea linkages. Such materials are typically prepared from the reaction of a diisocyanate and a polymer having a reactive portion (diol, diamine or hydroxyl and amine), and optionally, a chain extender.

Suitable diisocyanates include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate), isophorone diisocyanate (IPDI) and 4,4'-methylenebis(cyclohexyl isocyanate). A number of these diisocyanates are available from commercial sources such as Aldrich Chemical Company Milwaukee, Wis., USA) or can be readily prepared by standard synthetic methods using literature procedures.

The alcoholic or amine containing polymer can be a diol, a diamine or a combination thereof. The diol can be a poly(alkylene)diol, a polyester-based diol, or a polycarbonate diol. As used herein, the term "poly(alkylene)diol" refers to polymers of alkylene glycols such as poly(ethylene)diol, poly(propylene)diol and polytetramethylene ether diol. The term "polyester-based diol" refers to a polymer such as ethylene, 1,3-propylene, 1,2-propylene, 1,4-butylene, 2,2-dimethyl-1,3-propylene, and the like. One of skill in the art will also understand that the diester portion of the polymer can also vary. For example, the present disclosure also contemplates the use of succinic acid esters, glutaric acid esters and the like.

The polymers of the present disclosure may be combined with biofunctional substances. In particular, implants with a texture-induced bacteriostatic functionality may be beneficially augmented by addition of a bacteriocidal group. Examples of bacteriocides include silver sulfadiazine, chlorhexicline, glutaraldehyde, peracetic acid, sodium hypochlorite, phenols, phenolic compounds, iodophor compounds, quaternary ammonium compounds, and chlorine compounds, in addition to the clinically useful antibiotics.

Figure 3A:
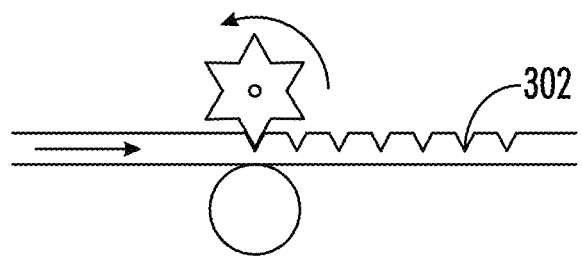
FIG. 3a,b. A method of manufacture of an implantable prosthetic of the present disclosure.
Figure 3B:
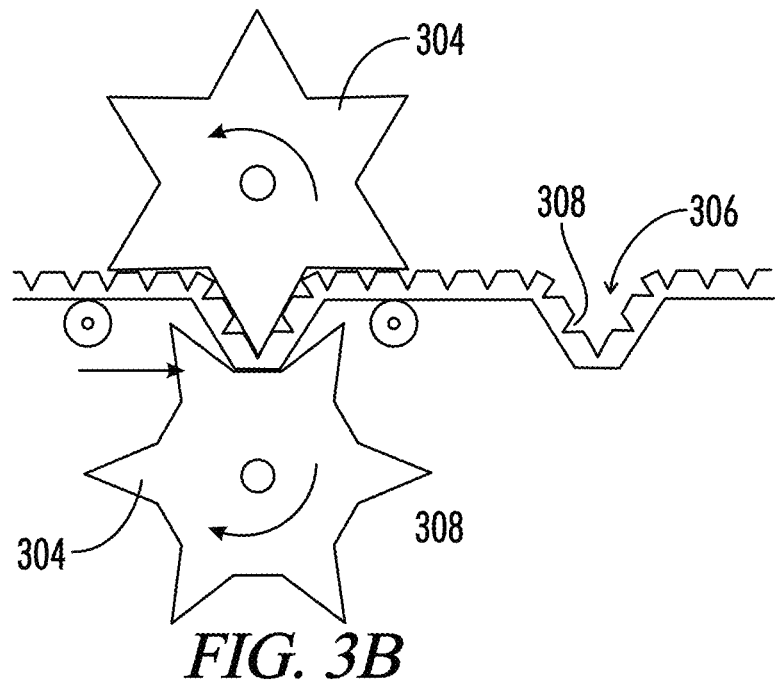

The methods of manufacture of the implantable prosthetics of the present disclosure include lithography, casting, extrusion/embossing, and any of several methods for transferring a texture to a surface. A preferred method is embossing. Referring now to FIG. 3, a polymeric substance is heated to a molten state and passed through dual rollers, at least one of which contains a negative image of the desired embossed structure. In the instance of FIG. 3, a nano-scale texture 302 is embossed on a formed planar sheet 300, as depicted in FIG. 3a. As depicted in FIG. 3b, formed sheet 300 is heated to a malleable but not fluid state and passed through dual rollers 304 possessing a micro-scale texture 306 which impresses an inverse image. The micro-scale texture 306 is large relative to the nano-scale texture 302, thus the impression of the micro-scale texture 306 folds the nano-scale texture 302, making possible involute structures 308 which would ordinarily not be possible with lithography or casting methods. The method depicted in FIG. 3 may be improved by heating from the non-textured side, so that the textured side is cooler and the nano-scale texture is less likely to be deformed by impressing the micro-scale texture over the nano-scale texture.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in implantable medical devices.

As used herein, the term "about" should be construed to refer to both of the numbers specified in any range. Any reference to a range should be considered as providing support for any subset within that range.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the embodiments disclosed herein. It is intended that the specification, together with the example, be considered to be exemplary only, with the scope and spirit of the disclosure being indicated by the claims which follow the example.

EXAMPLES

The following are examples. In these examples the following variables will be used to describe the surface texture. An upper case variable denotes that variable measured on a large scale, and a lower case variable denotes that variable measured on a smaller scale. By extrapolation, structures comprising more than two texture scales are anticipated. Height (H) is measured on the structure of largest connectedness (C) value, whether it be a positive (protuberance) or negative (valley) structure. The variables x and y denote orthogonal coordinates in the plane of a surface of the device or contacting tissue surface. A variable associated with another variable in parentheses denotes the first variable is a function of a second variable, for example F(x) denotes the fractal dimension varies as a function of the spatial dimension x.

H,h=height, measured orthogonal to the plane of the surface, peak to trough

D,d=diameter, measured in the plane of the surface, 2× lateral peak to trough, x and y values P,p=pitch, measured in the plane of the surface, peak to peak, x and y value F,f=fractal dimension R,r=corner radius, x and y values C,c=connectedness Example 1: D not Equal to P A regular array of protuberances or valleys with height H, wherein the diameter D of the protuberances or valleys is different from the spacing P between such structures.

Example 2: Sinusoidally Varying Height

A regular array of approximately conical protuberances or valleys with height H(x,y)=A sin(x,y), where sin(x,y) can denote any of sin(x)+sin(y), sin(x)sin(y), sin(xy), sin(x+y).

Example 3: D(x) and P=Constant

A regular array of approximately conical protuberances or valleys with varying diameter D(x,y)=A sin(xy) and constant distance between protuberances or valleys P.

Example 4: P(x) and D=Constant

A regular array of approximately conical protuberances or valleys with varying spacing P(x,y)=A sin(xy) and constant protuberance or valley diameter D.

Example 5: Koch Snowflake

The surface constructed by starting with an approximately conical protuberance or valley, then recursively altering each protuberance or valley as follows:
1. Draw two line segments, running peak to trough, intersecting the peak orthogonally (see FIG. 7A).
2. divide each line segment into three segments of equal length.
3. Place a conical protuberance or valley centered on each of the middle segments of step 2 (see FIG. 7B).
4. Repeat steps 1-3 on the protuberances or valleys of step 3 (see FIG. 7C). The resulting shape is shown in cross section in FIG. 7D with fractal dimension F=1.26.

Example 6: Sierpinski Gasket

Figure 4:
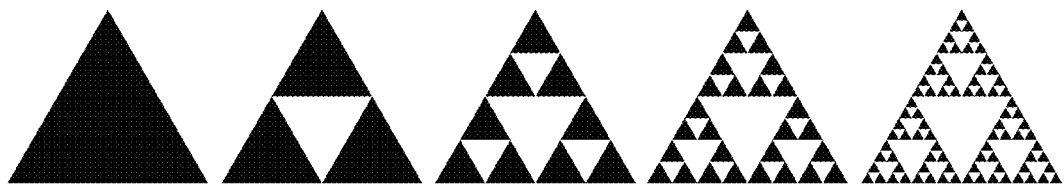
FIG. 4. Example of Sierpinski gasket surface texture.

An algorithm for obtaining arbitrarily close approximations to the Sierpinski triangle is as follows
1. Tile the implant surface with maximal sized triangles
2. Shrink the triangle to ½ height and ½ width, make three copies, and position the three shrunken triangles so that each triangle touches the two other triangles at a corner.
3. Note the emergence of the central hole (FIG. 4)
4. Apply step 2 to the largest remaining triangles Replace the triangles with either tetrahedrons or cones, either positive or negative (FIG. 4). The resulting structure has fractal dimension F=1.59.

Example 7: Apollonian Gasket

Figure 5:
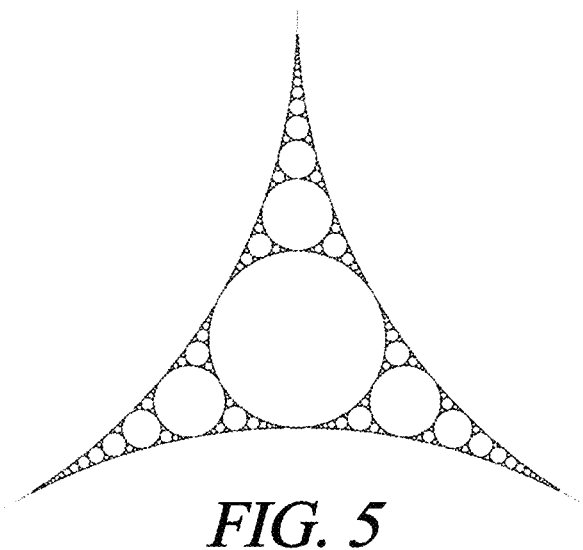
FIG. 5. Example of Apollonian gasket surface texture.

Tile the implant surface with three circles $C_1$, $C_2$ and $C_3$, each one of which is tangent to the other two (in the general construction, these three circles can be any size, as long as they have common tangents). Apollonius discovered that there are two other non-intersecting circles, $C_4$ and $C_5$, which have the property that they are tangent to all three of the original circles—these are called Apollonian circles. Adding the two Apollonian circles to the original three, we now have five circles (FIG. 5) Take one of the two Apollonian circles—say $C_4$. It is tangent to $C_1$ and $C_2$, so the triplet of circles a, $C_1$ and $C_2$ has its own two Apollonian circles. We already know one of these—it is $C_3$—but the other is a new circle $C_6$.

In a similar way we can construct another new circle $C_7$ that is tangent to $C_4$, $C_2$ and $C_3$, and another circle $C_8$ from $C_1$, $C_3$ and $C_1$. This gives us 3 new circles. We can construct another three new circles from $C_5$, giving six new circles altogether. Together with the circles $C_1$ to $C_5$, this gives a total of 11 circles. Continuing the construction stage by stage in this way, we can add $2 \cdot 3^n$ new circles at stage n, giving a total of $3^{n+1}++2$ circles after n stages. In the limit, this set of circles is an Apollonian gasket. The Apollonian gasket has a fractal dimension F=1.3057. The circles can be replaced with positive or negative cones.

Example 8: Diffusion Limited Aggregation

Figure 6:
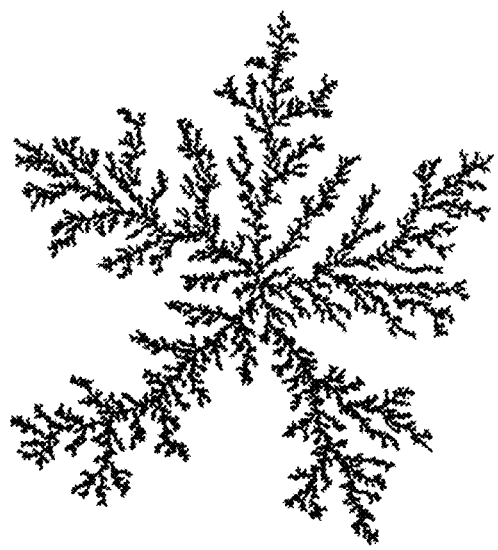
FIG. 6. Example of diffusion limited aggregation surface texture.

Partition the implant surface into an approximately circular grid of square cells. The cell at the center of the circle is the location of the seed point. Now pick a square on the perimeter of the grid and place a random function on that square. Randomly, advance the state of the function to one of the four adjacent squares. If this function leaves the implant surface another seed point is started, chosen randomly at the edge. When the function arrives at one of four squares adjacent to the seed point, it stops there forming a cluster of two seed points, each releasing a new function. Continuing in this way, builds an aggregate, illustrated in FIG. 6. Now replace the linear trace with either a protuberance or a valley, generally these structures are inscribed on a larger scale structure of conical protuberances or valleys.

Example 9: Absorbable Hydrophilic Implantables Made Hydrophobic to Reduce the Foreign Body Response The identification of a foreign body by cells in a mammalian body requires the adsorption of proteins that have been denatured by the foreign body. The adsorption of proteins trigger various cellular mechanisms for elimination or walling off of a foreign body. Hence, hydrophilic materials generally are more biocompatible and result in less fibrosis by reducing the degree of foreign body response. However, absorbable materials, even if they are relatively hydrophilic, can trigger foreign body response due to a constantly changing surface and the release of ionic species. In this example a trick is employed to activate protein denaturation without allowing its attachment to the implant.

The "hydrophobic effect" of hydrophobic materials is the dominant force for folding of globular protein in water. The folding occurs due to relatively hydrophobic side chains on protein molecules. The hydrophobic interaction is characterized in a large entropy gain, which typically results in the release of water molecules from the hydrophobic component with a relatively small enthalpy change. However, when a hydrophilic material possesses a surface texture that induces the hydrophobic effect the second part of the reaction, the release of water, is inhibited by polar interactions between water and the hydrophilic material.

Figure 8:
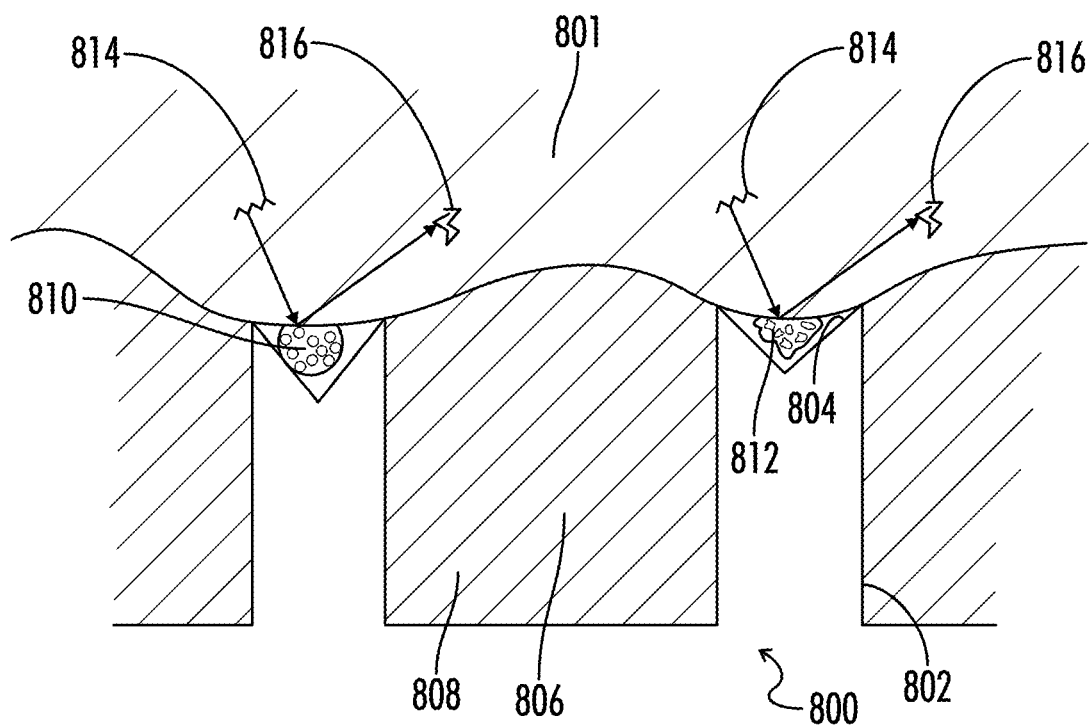
FIG. 8. Example of an absorbable hydrophilic implantable made hydrophobic to reduce a foreign body response.

Accordingly, two scales of protuberances, approximately pillar or conical are preferred. Referring to FIG. 8, a textured surface 800 interfaced with tissue 801 comprises first scale protuberances 802 and second scale protuberances 804. Water layer 806 fills the valleys 808 of the first scale. Air 810 and later lipids 812 surround the second scale features. Proteins 814 interact with the hydrophobic air 810 or lipid 812 tips and fold 816. Protein adsorption is inhibited by reduction of the surface energy of the textured surface 800, since water 806 is strongly held in the valleys 808.

Example 10: Absorbable Hydrophilic Implantables Made Hydrophobic to Reduce the Rate of Absorption The disclosure relates to implantable, absorbable sheets which are hydrophilic, and possibly swell or even dissolve in situ, whereby the addition of a hydrophobic structure reduces the rate of absorption or conformal change in situ.

Figure 9:
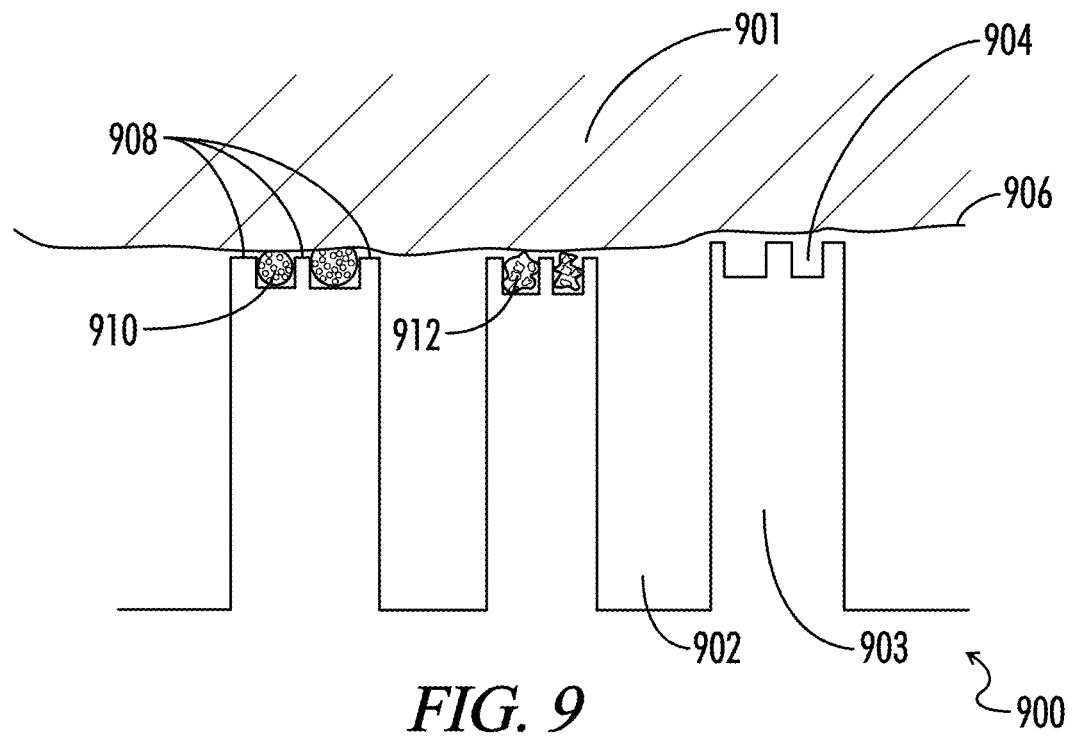
FIG. 9. Example of an absorbable hydrophilic implantable made hydrophobic to reduce the rate of absorption.

Accordingly, two scales of depressions, approximately cylindrical or conical are preferred. Referring to FIG. 9, a textured surface 900 interface with tissue 901 comprises first scale depressions 902 and first scale protuberances 903 and second scale depressions 904. Water layer 906 interacts only with ridges 908 formed by the first scale 902 and second scale 904 structures. Air 910 and later lipids 912 surround the second scale features. Thus the surface area presented to water is significantly reduced.

Example 11: Absorbable Hydrophobic Implantables Made Hydrophilic to Reduce the Foreign Body Response Alternatively, the disclosure relates to physiologically absorbable, generally fibrogenic, hydrophobic materials that are made relatively hydrophilic during a first interval by the addition of surface texture. Structures of this type resemble corals.

Figure 10:
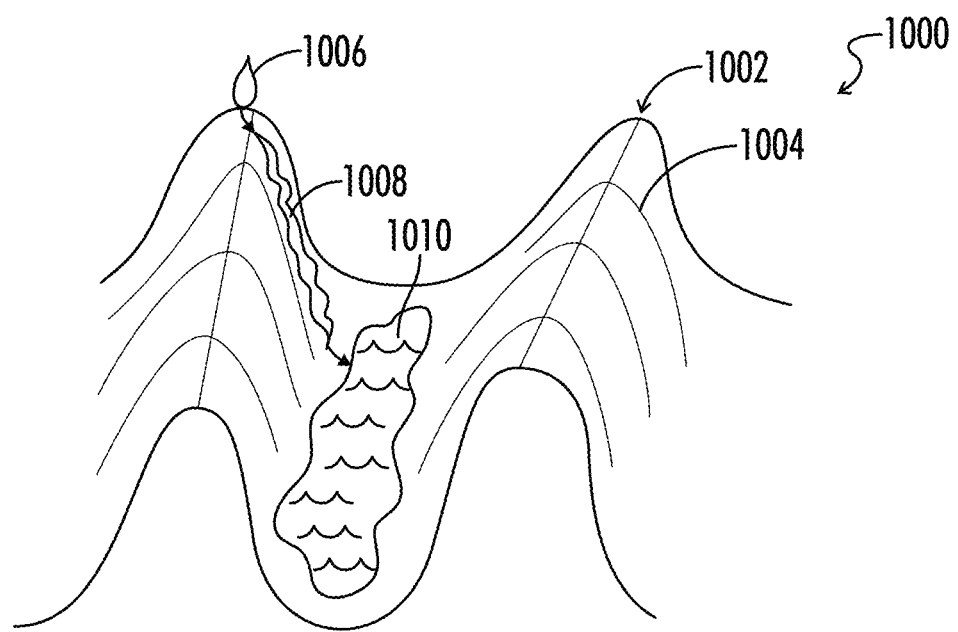
FIG. 10. Example of an absorbable hydrophobic implantable made hydrophilic to reduce a foreign body response.

Accordingly, two scales of ridges, with a high connectedness number and tortuosity are preferred. Referring to FIG. 10, a textured surface 1000 comprises first scale ridges 1002 and orthogonally arranged second scale ridges 1004. Water layer 1006 wicks 1008 first into small scale ridges 1004 which drains 1010 into large scale ridges 1002. Eventually the entire implant surface is coated with a thin layer of water, which without the surface texture would have been coated by protein.

Figure 11:
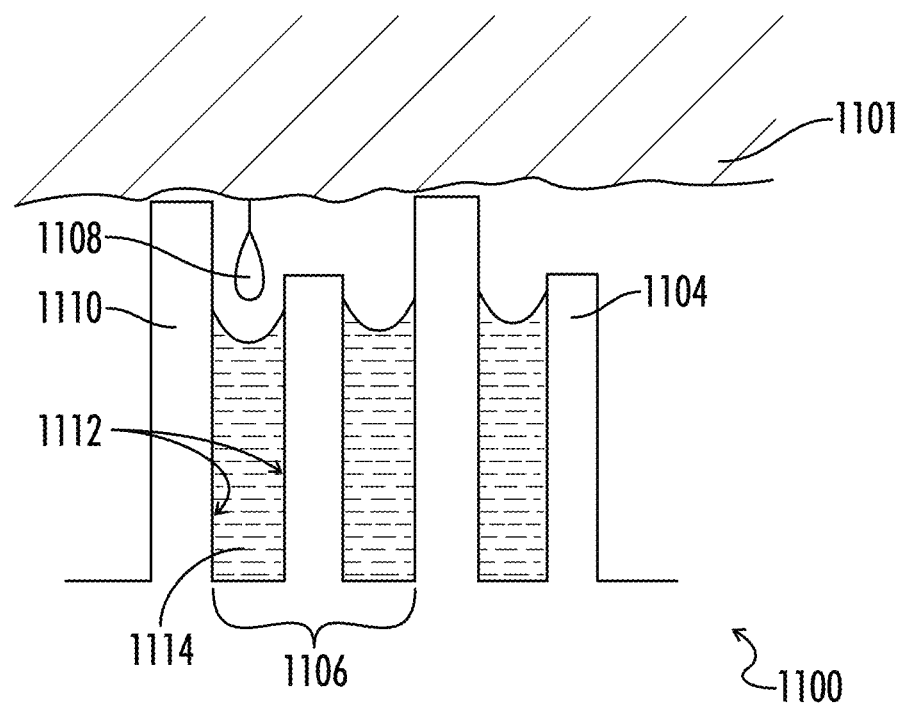
FIG. 11. Example of an absorbable hydrophobic implantable made hydrophilic to increase the rate of absorption.

Example 12: Absorbable Hydrophobic Implantables Made Hydrophilic to Increase the Rate of Absorption Alternatively, the disclosure relates to hydrophobic implantable sheets that do not absorb quickly in the body, which are made to absorb more quickly with the addition of a hydrophilic structure. Accordingly, two height scales of pillars are preferred. Referring to FIG. 11, a textured surface 1100 interacting with tissue 1001 comprises first scale pillars 1102 and between these second scale pillars 1104. The first scale pillars form spaces 1106 which induce a capillary effect 1108, and actively draw water 1108 into the spaces 1106 as the implant material dissolves into the water 1110. The second scale pillars 1104 form smaller spaces 1112 that further drive water 1114 deeper into the substrate. Hence, the surface area in contact with water is significantly increased.

Example 13: Implantables with One Side More Absorbable than the Other Side

An implant with one side with a surface texture of EXAMPLE 10 and the other side with a surface texture of EXAMPLE 12 is provided.

Example 14: Implantables with One Side More Resistant to Adhesion than the Other An implant with one side with a surface texture of EXAMPLE 9 and the other side with a surface texture of EXAMPLE 11 is provided.

Example 15: Implantables with at Least One Side Immediately Tissue Adhesive

Surgical barrier implants block tissue adhesions between adjacent layers of tissue. Due to their anti-adhesive functionality, they tend to migrate after implanted requiring localization by suture or staple. These localization points then become foci for tissue adhesion. A combination of Wenzel and Cassie states creates a Cassie wetting condition characterized by a large contact angle hysteresis. Accordingly, these textures are not energetically favored to slide across a surface.

Figure 12:
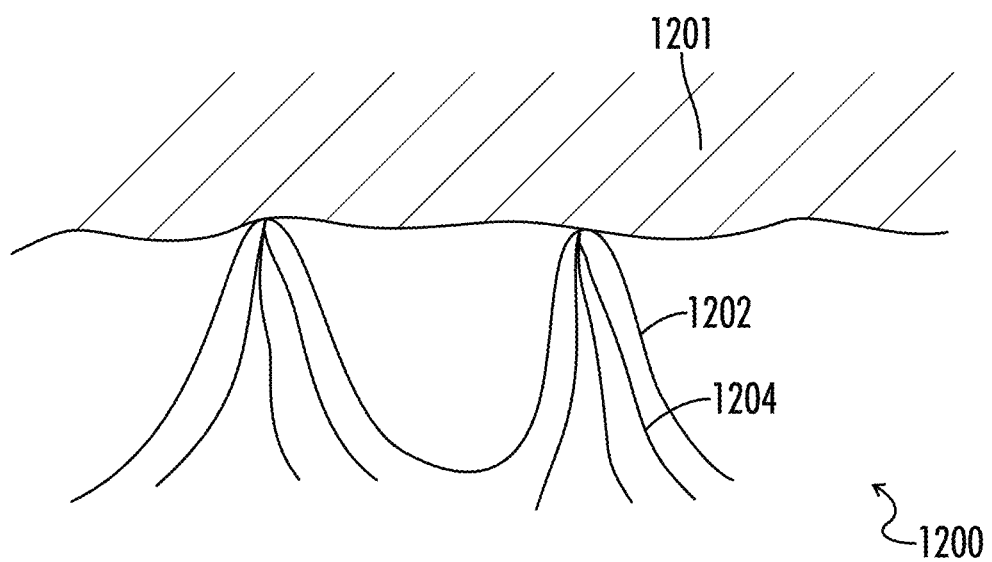
FIG. 12. Example of an implantable with at least one side immediately tissue adhesive.

Referring to FIG. 12, a Cassie wetting texture 1200 interacting with tissue 1201 is comprised of first scale protuberances 1202 and second scale ridges 1204 oriented axially with protuberances 1202 and distributed circumferentially. The ridges 1204 enter the Wenzel state when placed on tissue. The Wenzel state is prevented from moving in the plane of the implant by the adjacent Cassie states created by the protuberances 1202.

Example 16: Implantables with Lipophilic/Hydrophilic Filter Effect Surface

For example, a surface filtering effect wherein a first substance or structure is brought into more intimate contact with the implant than another substance or structure. The intimacy defined by the spatial scale of interactions. An implant with the surface texture of EXAMPLE 14, wherein the implant substrate is strongly hydrophobic, such that the large scale Cassie structures preferentially fill with lipids and the small scale Wenzel structures preferentially fill with water. Accordingly, in the thin interfacial layer between implant and tissue, the heterogeneous liquid comprised of water and lipids segments separate such that the water fraction is localized to the Wenzel sites and the lipid fraction is localized to the Cassie sites.

Example 17: Implantables with Cell Type Filter Effect Surface

According to the differential adhesion hypothesis (sometimes called the "thermodynamic hypothesis") heterotypic cells in mixed aggregates can sort out into isotypic territories based on surface chemistry and texture. The hypothesis treats tissue as a viscoelastic liquid, and as such each cell type possesses a characteristic tissue surface tension. The differing surface tensions give rise to a sorting behavior. Tissue type with a higher surface tension occupy an internal position on the implant surface relative to a tissue with a lower surface tension. Quantitative differences in homo and heterotypic adhesion are supposed to be sufficient to account for this phenomenon without the need to postulate cell type specific adhesion systems.

This property can be applied to bacterial species as well as cell types. So where a certain cell type is desired and other cell types not desire, the surface texture can be impressed with the appropriate surface energy signature. For example, in an application where inflammatory cells such as macrophages, giant cells, generally of a spherical shape are to be excluded in favor of generally cylindrical cells such as muscle cells and endothelial cells. The cylindrical cells typically possess a higher surface tension than the spherical cells. Accordingly, we can create a sorting surface with a generally more axial structure than a spherical structure, such that cylindrical cells are energetically favored for attachment.

Figure 13:
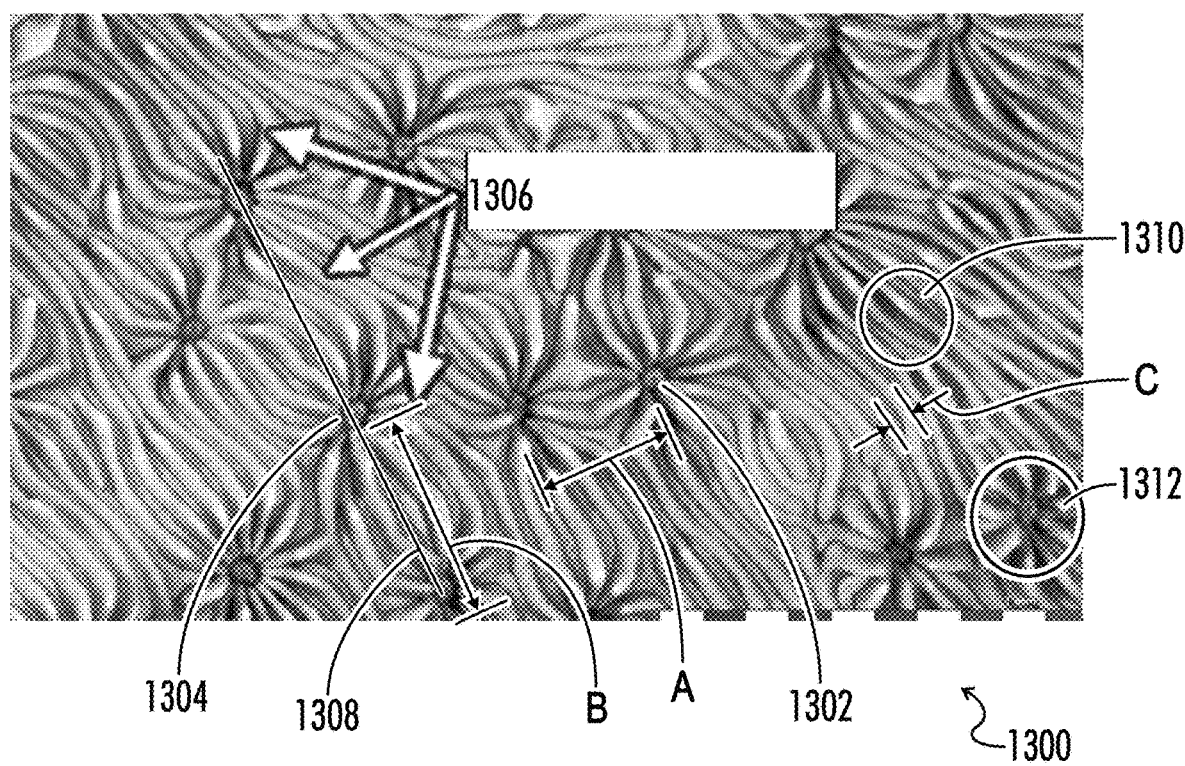
FIG. 13. Example of an implantable with cell type filter effect surface.

Referring to FIG. 13, a cell sorting surface 1300 is comprised of centers 1302 that are generally semi-spherical protuberances with a central dimple 1304 and radial, closely spaced ridges 1306. The centers 1302—are arranged in rows 1308 separated by a first characteristic distance A. The centers 1302—within a row 1308 are regularly spaced a second characteristic distance B. The distance between ridges 1306 is a third characteristic dimension C. A combination of characteristic distances A, B, C determines which cell type associates with the implant surface.

The centers 1302 are connected by ridges 1306 with orthogonal smaller scale ridges. The larger scale ridges 1306 are arranged to approximate equal distance spacing. This results in a parallel structure 1310 in the space between centers 1302 and a radial structure 1312 in the space proximal to centers 1302. The centers 1302 are connected by ridges 1306. The connectivity is characteristically directed, for example in the direction of row 1308, but they could also be directed orthogonally, and diagonally.

Example 18: Implantables with a Tissue Type Filter Effect Surface

On at least one side of a sheet implant, texture is disposed, such that relatively hydrophobic tissue structures are attracted and hydrophilic tissue structures are repelled. For example, the relatively hydrophobic tissue constituents of protein and fat are attracted and hydrophilic structure such as serum, exudate, and the generally lubricating and largely aqueous constituents are repelled so as to localize an implant in situ.

Figure 14:
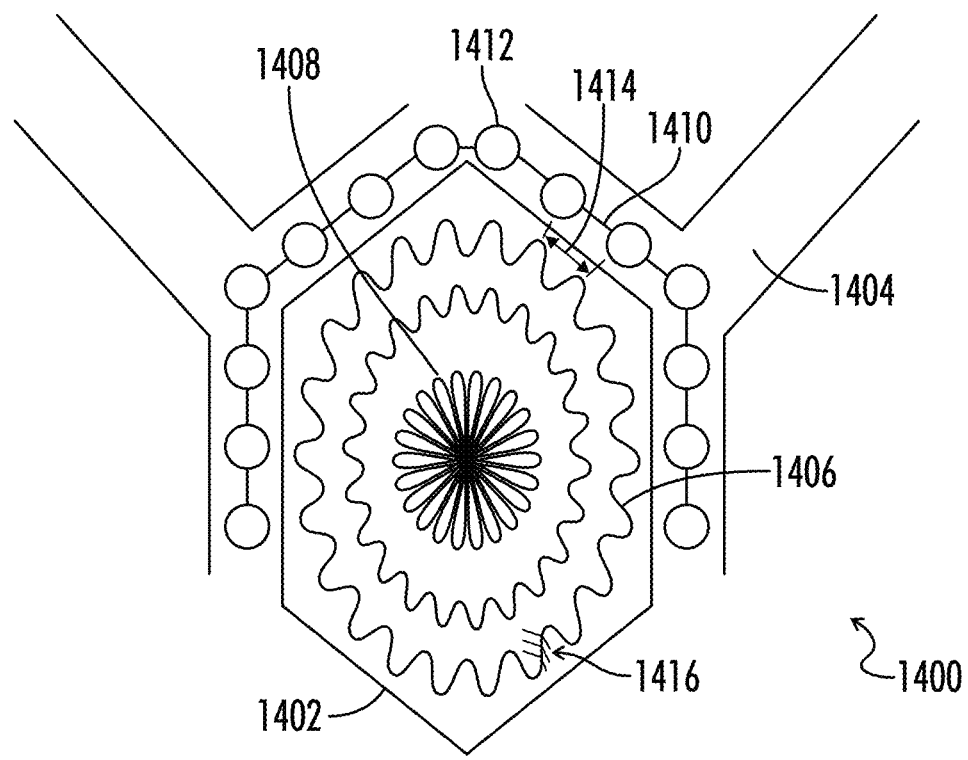
FIG. 14. Example of an implantable with a tissue type filter effect surface.

Referring to FIG. 14, textured surface 1400 comprises hexagonal depressions 1402—separated by relative narrow ridges 1404. The interior of depression 1402 rapidly becomes circular on its surface on which are placed a multiplicity of equally space, concentric, undulating concentric ridges 1406 with a generally circular profile. At center is a petal structure 1408—with the number of petals corresponding to the number of cycles in the adjacent ridge structure 1406. On the ridges 1404 is a circumferential ridge 1510 broken into circular ridges 1512, the circular ridges 1412 corresponding to a period 1414 of adjacent undulating ridges 1406. The space between ridges 1406 may be optionally ornamented with orthogonal fine scale ridge structures 1416.

Example 19: Implantables with a Bacterial Adhesion Resistance

Biomaterials and medical devices immediately and spontaneously acquire a layer of host proteins prior to interacting with host cells and microbes. In this example, attention is directed to limiting microbial adhesion, but the principle can be equally applied to reduced tissue adhesion surfaces.

The types, levels, and surface conformations of the adsorbed proteins are critical determinants of what kind of living substances adheres to the implant surface. Conversely, the types, concentrations, and conformations of these surface-adsorbed proteins are dependent on biomaterial surface properties that dictate the adhesion and survival of cells, especially microbes, monocytes, and macrophages. The interaction of adsorbed proteins with adhesion receptors present on microbes and inflammatory cell populations constitutes the major recognition system of biologics to implantable synthetic materials. The presence of adsorbed proteins such as albumin, fibrinogen, complement, fibronectin, vitronectin, $\gamma$ globulin, and others mediate microbial colonization, inflammatory cell interactions and tissue adhesion. It is not surprising that microbial colonization is linked to inflammatory and wound healing processes. The signaling adsorbed proteins may also desorb spontaneously, i.e. the Vroman effect. The sequence of protein adsorptions/desorbtions is a sequence to which microbes have evolve to recognize and exploit.

Major driving forces behind protein adsorption include: surface energy, intermolecular forces, hydrophobicity, and ionic or electrostatic interaction—all of which are modified by surface texture. The four fundamental classes of forces and interaction in protein adsorption are: 1) ionic or electrostatic interaction, 2) hydrogen bonding, 3) hydrophobic interaction (largely entropically driven), and 4) interactions of charge-transfer or particle electron donor/acceptor type.

Apart from the signaling aspects of foreign bodies in situ, cellular/bacterial adhesion is largely mediated by surface energy. That is to say, initiating a response is insufficient to maintain a response. The goal of a bacterial resistant implant is to shift the surface energy equations, to promote affinity of bacteria to bind to tissue or themselves. Binding to tissue needs to be energetically favored over binding to the implant surface. More particularly, if microbes should colonize the implant surface the spreading of a protective biofilm is preferably energetically disfavored. In a disfavored scenario, an evolving biofilm tends to take on a spherical shape, which turns the biofilm surface to encapsulate the bacterial colony and decrease the contact area of the bacterial colony with the implant surface.

Figure 15:
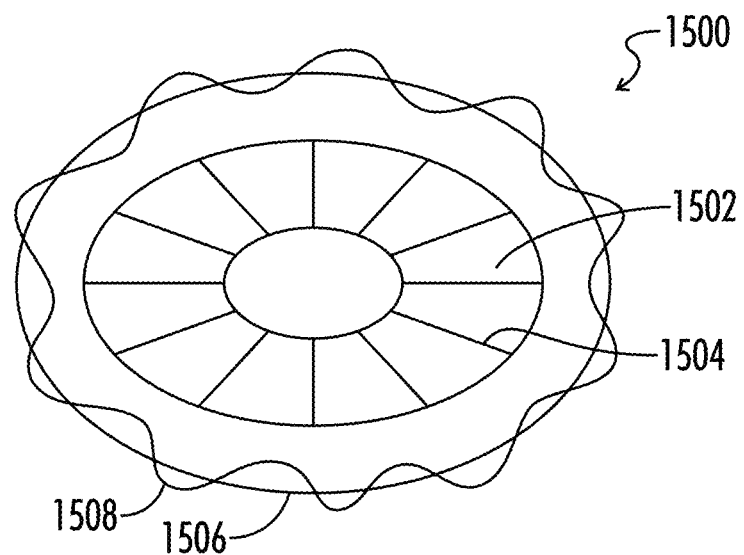
FIG. 15. Example of an implantable with a bacterial adhesion resistance.

While many of the prior examples possess bacteriostatic or bacterio-anti-adhesive functionality, referring to FIG. 15, a preferred embodiment is described. The anti-microbial surface 1500 is comprised of multiple depressions 1502 which may be any conformation, e.g., cylindrical, conical, square, hexagonal. The interior surface of the depressions 1502 are ornamented with nano-scale structures that maximize the hydrophobicity and minimize the surface energy, such that while microbial attachment is preferred in the depressions because they shield the microbes from macrophages, the surface energy is so reduced within the depressions that the microbes are only tenuously adhered. Furthermore, attachment of microbes within the depressions changes the local surface energy and directs macrophages to the occupied depression. Accordingly, a macrophage can easily infiltrate the depressions and eliminate the nascent microbial colony. The nanoscale structures are ridges 1504 circumferentially and axially arranged, these surfaces enhance the hydrophobicity of the interior surfaces of depressions 1502. Surrounding the depressions 1502 are circular ridges 1506 embossed with sinusoidal ridges 1508. The sinusoidal structure mitigates a circular contact interface (low energy) between a biogel evolving out of depressions 1502 and the implant surface, thus making it energetically disfavored and unstable. In particular, propagation of the biofilm is inhibited. The regions between depressions circumscribed by sinusoidal ridges may be ornamented with any of the above examples.

Example 20: Implantables with a Bacterial Adhesion Resistance

An anti-microbial surface wherein the surface filter effect is employed, wherein one species characterized by scale or polarity is excluded and another species characterized by scale or polarity is attracted, or both are excluded, or both are attracted, on the same side or on opposite sides of a sheet implant. For example an implant side in which bacteria are excluded and a component of tissue is attracted and on the other side bacteria are excluded and a component of tissue is excluded.

Example 21

The implant made from the above examples wherein the substrate is porous with three dimensionally interconnected pores, some of which are representative of the above structures.

Example 22

Any implant of the above where the texture is deployed in a step-like contour.

Example 23

Any of the above implants possessing a semi-open structure wherein hierarchical texture is located on cross elements, such that the semi-open structure itself comprises a texture.

Example 24

Any of the above implants with fibers imbedded and protruding from the polymer substrate, said fibers can be bifurcated on a number of spatial scales in the manner of the fibers disposed on a Gecko foot.

Example 25

Any of the above implants with fibers attached by both ends in the polymeric substrate, thus determining loops, the radius of said loops of at least two length scales.

Example 26 Efficacy Studies

The following are efficacy studies carried out on petal structures of the present disclosure, in particular regarding adhesivity. A number of casting materials were tested, including: hot wax, wax in toluene, nail polish, hot glue, cyanoacrylate, plaster, PLA 708 (Boehringer-Ingelheim) and pyroxylin. Only the latter two were successful, the pyroxylin being the most dependable in terms of reproducing the petal surface.

A limited shear test was performed with a small quantity of positive image PLA sheets. The procedure consisted of forming a negative pyroxylin cast, pouring PLA acetone solution over the negative cast, and dissolving away with ethanol the pyroxylin portion.

In the microscopic analysis, it was extremely difficult to view the petal structure in the pristine cast state. Red food coloring only created beads on the surface which were opaque to imaging. The red food coloring was then mixed with an amphiphilic surfactant, Triton X, which possesses both hydrophobic and hydrophilic ends, and thus can orient to suit the surface with which it is interacting. This produced extremely interesting results.

The number of variables of interest in this study are numerous, and the test articles difficult to manufacture. However, these are the variables that were studied with sufficient statistical power: negative Vs positive texture, pyroxylin Vs PLA (pyroxylin is less hydrophobic than PLA), kinetic Vs static shear, under water Vs wet.

In preliminary testing, it was discovered that the peal strength is extremely low. Attempts to measure peal strength failed. The difference in peal strength between a smooth surface of a given material and a petal textured surface was noticeable, but not measurable with available equipment. The strength in all cases would be less than 1 g. However, the shear strength was significant. Therefore, it became apparent that it was important to make sure that orthogonal forces were not applied to the test article during shear evaluation. Accordingly, a 1 cm disc was constructed with a weight of approximately 0.5 g on to which a test article was mounted with cyanoacrylate. This ensured the test article did not experience orthogonal forces. The discovery that the peal strength is exceptionally low is not surprising given that it is far easier to pluck a droplet from a petal surface than roll in across its surface. Clinically, this would not be a problem since once an operative site is closed there is an abundance of orthogonal pressures which likely will greatly enhance the resistance to shear. The effect on shear strength for smooth surfaces is quite different, applied orthogonal force increases the resistance to shear only linearly and not parabolic as seen in initial petal tests. Thus there was no need to test smooth surface differences between pyroxylin and PLA.

Mechanical localization characteristics were assessed. Cutlets of bovine "steak" were purchased and sliced into 3 cm cubes and affixed to a localized platform. The meat was kept well hydrated with physiologic saline solution at 22° C. Test articles were cut to 1×1 cm squares and mounted on discs to which was attached the filament through which force would be applied to the test article. Shear was measured by placing the strip on the 3 cm cube of meat and pulling horizontally to the surface. Thus these measurements yield a force per unit area (1 cm2).

In preliminary testing, there was no difference in shear force immediately Vs 1 hour later. Thus there was no observable saturation effect, and shears were not measured at different time intervals.

Two wetting scenarios were tested. In one scenario, the tissue surface was kept moist to replicate normal surgical conditions (wet to touch), but no standing water. In another, the tissue and test articles were immersed in water. The buoyancy of the disc support was minimal. However, a rather more complicate pulley system was employed for testing in water, which in the worst case should result in lower shear forces since the resistance to shear would be communicated less efficiently to the sensor, and thus the force measured lower.

In all measurements, clear outliers were discarded, and when possible the run was repeated with additional test articles.

An Instron Mini 55 was used to record force and the crosshead speed was 0.1 cm/sec. The load cell limit was 200 g with an accuracy of +/−0.1 g. Pull tests:

All measurement rounded to nearest gram. All measurements were done with a 0.5 gram disc. All measurements were done with fresh casts to avoid texture filling, but variations in thickness could contribute to variable changes. Whenever possible, experiments comparing different attributes were done with casting made at the same time to avoid changes in casting solution or ambient conditions. Results are depicted in tables 1-4.

TABLE 1

Negative Vs Positive

| Texture | Shear (submerged in water) (grams force) |
|---|---|
| Negative (PLA) N = 3 | 105 +/− 36 |
| Positive (PLA) N = 3 | 37 +/− 12 |

TABLE 2

Pyroxylin Vs PLA

| Texture (negative) | Shear (submerged in water) (grams force) |
|---|---|
| Pyloxyrin (N = 5) | 79 +/− 32 |
| PLA (N = 5) | 107 +/− 35 |

TABLE 3

Kinetic Vs Static

| Texture (negative, PLA) | Shear (submerged in water) (grams force) |
|---|---|
| kinetic (N = 10) | 101 +/− 22 |
| Static (N = 10) | 119 +/− 35 |

TABLE 4

| Texture (negative, PLA) | Shear (wet) (grams force) |
|---|---|
| kinetic (N = 10) | 27 +/− 11 |
| Static (N = 10) | 32 +/− 9 |

What is claimed is:

1. A medical device comprising a substrate, the substrate including hierarchical surface texture wherein the hierarchical surface texture comprises at least a first surface texture and a second surface texture, the at least second surface texture being disposed about the at least first surface texture, wherein the hierarchical surface texture is configured to form an interface with liquids present in a host tissue, at least one of the at least first surface texture or second surface texture is configured to trap air between the device and the host tissue; the other at least first or at least second surface texture is configured to not trap air between the device and the host tissue, at least one of the at least first surface texture or second surface texture comprises absorbable material, wherein the at least one surface texture is modified by absorption, such that the at least one surface texture becomes more wetting or less wetting as the medical device is absorbed; and wherein the interface includes a contact hysteresis angle of at least 5 degrees.

2. The medical device of claim 1, wherein after a period of time, the interface comprises: a) a solid hydrophilic phase, b) a liquid hydrophobic phase, and c) a liquid hydrophilic phase.

3. The medical device of claim 1, wherein the trapped air is replaced by a liquid hydrophobic phase after a period of time.

4. The medical device of claim 1, wherein the hierarchical surface texture comprises hydrophilic absorbable material, wherein the hydrophilic absorbable material is made less hydrophilic by the hierarchical surface texture, and the hierarchical surface texture reduces a rate of absorption or conformal change of the medical device in the host tissue.

5. The medical device of claim 1, wherein the hierarchical surface texture comprises hydrophobic absorbable material, wherein the hydrophobic absorbable material is made less hydrophobic by the hierarchical surface texture, and the hierarchical surface texture increases a rate of absorption or conformal change of the medical device in the host tissue.

6. The medical device of claim 1, wherein the hierarchical surface texture has a rate of absorbance in the host tissue that mitigates tissue adhesion, bacterial colonization, and/or biofilm formation during a first time interval, and wherein the hierarchical surface texture becomes a smooth, hydrophilic, rapidly absorbing and non-fibrogenic surface during a second time interval.

7. The medical device of claim 1, wherein the at least second surface texture comprises a pitch of 10 nanometers to 1 micron, and the at least first surface texture comprises a pitch of 2 microns to 100 microns, wherein the hierarchical surface texture is configured such that a first portion excludes attachment of a first tissue species and a second portion promotes attachment of a second tissue species.

8. The medical device of claim 7, wherein the first tissue species is a microbe and the second tissue species is a host cell.

9. The medical device of claim 7, wherein the first tissue species is a protein and the second tissue species is a host tissue.

10. The medical device of claim 7 wherein the first tissue species is host tissue and the second tissue species is an endothelial cell.

11. The medical device of claim 1, wherein upon implantation in the host tissue, a surface charge of at least one of the first surface texture or second surface texture increases such that water is more strongly bonded to the substrate surface, but not so strongly bonded so as to preclude exchange of water molecules bonded to the substrate with surrounding water in the host tissue.

12. The medical device of claim 11, wherein the hierarchical surface texture is configured such that a layer of water adheres to the hierarchical surface texture and reduces a rate of protein molecule adsorption to the hierarchical textured surface relative to a device without hierarchical surface textures.

13. The medical device of claim 1, wherein the substrate is porous.

14. The medical device of claim 1, wherein the at least first surface texture forms a Cassie state when in contact with host tissue and the at least second surface texture forms a Wenzel state when in contact with host tissue.

15. The medical device of claim 1, wherein at least one of the first surface texture or second surface texture comprises a Koch snowflake pattern.

16. The medical device of claim 1, wherein at least one of the first surface texture or second surface texture comprises a Sierpinski gasket pattern.

17. The medical device of claim 1 wherein at least one of the first surface texture or second surface texture comprises an Apollonian gasket pattern.

18. The medical device of claim 1, wherein at least one of the first surface texture or second surface texture comprises a diffusion limited aggregation pattern.

19. A medical device comprising a substrate, the substrate having two sides, each of the two sides comprising hierarchical surface texture, wherein the hierarchical surface texture on each side is configured such that each of the hierarchical surface texture forms an interface with liquids present in a host tissue, wherein at least one portion of the hierarchical surface texture traps air between the device and tissue and at least a second portion of the hierarchical surface texture does not trap air between the device and tissue, and wherein the resulting interface generates a contact hysteresis angle of at least 5 degrees on one side of the substrate and less than 5 degrees on the other side of the substrate.

\* \* \* \* \*